United States Patent
Zhang et al.

(10) Patent No.: US 11,434,223 B2
(45) Date of Patent: Sep. 6, 2022

(54) NITROGEN HETEROCYCLIC COMPOUND, DISPLAY PANEL AND DISPLAY APPARATUS

(71) Applicant: WuHan TianMa Micro-Electronics Co., Ltd., Wuhan (CN)

(72) Inventors: Lei Zhang, Wuhan (CN); Wei Gao, Wuhan (CN); Qing Zhu, Wuhan (CN); Jinghua Niu, Wuhan (CN)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 412 days.

(21) Appl. No.: 16/242,302

(22) Filed: Jan. 8, 2019

(65) Prior Publication Data
US 2020/0095224 A1   Mar. 26, 2020

(30) Foreign Application Priority Data
Sep. 25, 2018   (CN) .......................... 201811115696.7

(51) Int. Cl.
*C07D 213/06* (2006.01)
*C07D 239/26* (2006.01)
(Continued)

(52) U.S. Cl.
CPC ......... *C07D 401/14* (2013.01); *C07D 213/06* (2013.01); *C07D 239/26* (2013.01);
(Continued)

(58) Field of Classification Search
None
See application file for complete search history.

(56) References Cited

U.S. PATENT DOCUMENTS

| 10,882,850 B2 * | 1/2021 | Zhang ................. C07D 403/14 |
| 2010/0090588 A1 * | 4/2010 | Yokoyama ........... C07D 417/14 |
| | | 313/504 |

(Continued)

FOREIGN PATENT DOCUMENTS

| CN | 101506197 A | 8/2009 |
| CN | 103325950 A | 9/2013 |

(Continued)

OTHER PUBLICATIONS

SciFinder Search (Mar. 9, 2021).*

(Continued)

*Primary Examiner* — Vu A Nguyen
(74) *Attorney, Agent, or Firm* — Tarolli, Sundheim, Covell & Tummino LLP

(57) ABSTRACT

A nitrogen heterocyclic compound having a structure of Chemical Formula I is provided. z is 1 or 2, m and n are each 1 or 2, p and q are each 0, 1 or 2. $X_1$-$X_6$ are each independently nitrogen or carbon, and at least one of $X_1$-$X_6$ is nitrogen. $R_1$, $R_2$ and $R_3$ are each independently C1-C10 linear or branched alkyl, substituted or unsubstituted aryl, fused aryl, an aromatic heterocyclic group, or a fused aromatic heterocyclic group. $R_1$ and $R_2$ may be otherwise a single bond. $Ar_1$ and $Ar_2$ are each substituted or unsubstituted aryl, fused aryl, an aromatic heterocyclic group, or a fused aromatic heterocyclic group. The nitrogen heterocyclic compound has a higher refractive index, can improve light extraction efficiency and luminous efficiency and alleviate angular dependence of luminescence when it is used as a capping layer CPL of an OLED device.

(Continued)

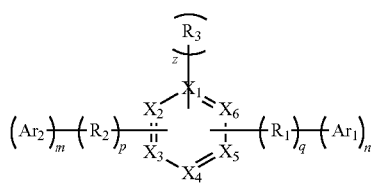

6 Claims, 3 Drawing Sheets

(51) Int. Cl.
| | | |
|---|---|---|
| *C07D 401/04* | (2006.01) | |
| *C07D 401/10* | (2006.01) | |
| *C07D 401/14* | (2006.01) | |
| *C07D 471/04* | (2006.01) | |
| *C07D 519/00* | (2006.01) | |
| *H01L 51/00* | (2006.01) | |
| *H01L 51/50* | (2006.01) | |

(52) U.S. Cl.
CPC ......... *C07D 401/04* (2013.01); *C07D 401/10* (2013.01); *C07D 471/04* (2013.01); *C07D 519/00* (2013.01); *H01L 51/0067* (2013.01); *H01L 51/0072* (2013.01); *H01L 51/5012* (2013.01); *H01L 51/5056* (2013.01); *H01L 51/5072* (2013.01)

(56) References Cited

U.S. PATENT DOCUMENTS

| | | | | |
|---|---|---|---|---|
| 2013/0248830 | A1* | 9/2013 | Welsh | H01L 51/0058 257/40 |
| 2015/0318487 | A1* | 11/2015 | Ito | H01L 51/508 257/40 |
| 2016/0190471 | A1* | 6/2016 | Inoue | C09K 11/06 257/40 |
| 2017/0244043 | A1* | 8/2017 | Kim | H01L 51/0085 |
| 2018/0331298 | A1* | 11/2018 | Hayashi | H01L 51/0054 |

FOREIGN PATENT DOCUMENTS

| | | | |
|---|---|---|---|
| CN | 103923065 A | 7/2014 | |
| CN | 105732588 A | 7/2016 | |
| CN | 106946859 A | 7/2017 | |
| CN | 107093677 A | 8/2017 | |
| CN | 107417668 A | 12/2017 | |
| CN | 108026079 A | 5/2018 | |
| CN | 108129386 A | 6/2018 | |
| CN | 108352454 A | 7/2018 | |
| CN | 109384802 A | 2/2019 | |
| CN | 111149229 A | 5/2020 | |
| KR | 20180103021 A | 9/2018 | |
| WO | WO-2017073594 A1 * | 5/2017 | ........... C07C 211/58 |

OTHER PUBLICATIONS

Varughese et al., Crystal Growth and Design, vol. 10, No. 6, 2010, 2571-2580.*
Chinese Office Action dated Jun. 23, 2021 for corresponding Chinese Application No. 201811115696.7.
Chinese Office Action dated Nov. 29, 2021 for corresponding CN Application No. 201811115696.7.

* cited by examiner

NITROGEN HETEROCYCLIC COMPOUND, DISPLAY PANEL AND DISPLAY APPARATUS

CROSS-REFERENCE TO RELATED APPLICATIONS

The present disclosure claims priority to Chinese Patent Application No. 201811115696.7, filed on Sep. 25, 2018, the content of which is incorporated herein by reference in its entirety.

TECHNICAL FIELD

The present disclosure relates to the field of organic electroluminescent materials, and in particular, to a nitrogen heterocyclic compound, and a display panel and a display apparatus comprising the nitrogen heterocyclic compound.

BACKGROUND

OLED has made great progress after several decades of development. Although an internal quantum efficiency of the OLED is close to 100%, an external quantum efficiency of the OLED is only about 20%. Most of light is confined inside a light-emitting device due to surface plasma loss and waveguide effect, resulting in a large energy loss.

In a top emission device, an organic capping layer (CPL) is usually deposited on a translucent metal electrode A1 to adjust an optical interference distance, suppress external light reflection, and suppress extinction caused by movement of surface plasma, thereby enhancing extraction efficiency of the light, and improving luminous efficiency. The existing CPL materials are mostly aromatic amine derivatives, phosphoxy derivatives and quinolinone derivatives, etc., which have both a hole transmission function and an electron transmission function and then improve the light extraction efficiency to some extent. However, the refractive index of the existing CPL materials is generally below 1.9, which does not meet the requirements of high refractive index; amine derivatives of specific structures having high refractive index and materials having specific parameters can improve the light extraction efficiency, but cannot solve the problem of luminous efficiency, especially for blue light-emitting elements. In order to increase the density of molecules and achieve high thermal stability, the designed molecules in the related art are big and loose, and cannot be closely packed, causing too many molecular gel holes during evaporation and poor coverage tightness. Therefore, there is a need to develop a new type of CPL material to enhance performances of OLED devices.

SUMMARY

The present disclosure is to provide a series of novel nitrogen heterocyclic compounds with a nitrogen heterocyclic structure as a center skeleton.

In an aspect, the present disclosure provides a nitrogen heterocyclic compound, having a structure represented by Chemical Formula I:

Chemical Formula I

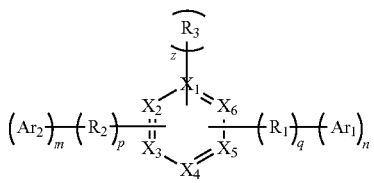

where z is 1 or 2, m and n are each 1 or 2, and p and q are each 0, 1, or 2;

$X_1$-$X_6$ are each independently nitrogen or carbon, and at least one of $X_1$-$X_6$ is nitrogen;

$R_1$ and $R_2$ are each independently a single bond, C1-C10 linear or branched alkyl, substituted or unsubstituted phenyl, substituted or unsubstituted diphenyl, substituted or unsubstituted terphenyl, substituted or unsubstituted naphthyl, substituted or unsubstituted anthracyl, substituted or unsubstituted acenaphthylenyl, or a substituted or unsubstituted C4-C40 aromatic heterocyclic group selected from a group consisting of pyridyl, thienyl, thiazolyl, thiadiazolyl, furyl, oxazolyl, and oxadiazolyl;

$R_3$ is C1-C10 linear or branched alkyl, substituted or unsubstituted phenyl, substituted or unsubstituted diphenyl, substituted or unsubstituted terphenyl, substituted or unsubstituted naphthyl, substituted or unsubstituted anthracyl, dimethyl fluorenyl, spiro fluorenyl, substituted or unsubstituted acenaphthylenyl, or a substituted or unsubstituted aromatic heterocyclic group selected from a group consisting of pyridyl, thienyl, thiazolyl, thiadiazolyl, furyl, oxazolyl, and oxadiazolyl; and $Ar_1$ and $Ar_2$ are each independently selected from a group consisting of substituted or unsubstituted phenyl, substituted or unsubstituted biphenyl, substituted or unsubstituted naphthyl, substituted or unsubstituted anthracyl, substituted or unsubstituted phenanthryl, substituted or unsubstituted triphenylenyl, substituted or unsubstituted acenaphthylenyl, substituted or unsubstituted pyrenyl, substituted or unsubstituted perylenyl, substituted or unsubstituted fluorenyl, substituted or unsubstituted spirobifluorenyl, substituted or unsubstituted chrysenyl, substituted or unsubstituted benzanthracenyl, substituted or unsubstituted fluoranthenyl, substituted or unsubstituted picenyl, substituted or unsubstituted pyridyl, substituted or unsubstituted pyrimidinyl, substituted or unsubstituted quinolyl, substituted or unsubstituted quinoxalinyl, substituted or unsubstituted phenanthrolinyl, substituted or unsubstituted benzophenanthrolinyl, substituted or unsubstituted furyl, substituted or unsubstituted benzofuranyl, substituted or unsubstituted dibenzofuranyl, substituted or unsubstituted thiophenyl, substituted or unsubstituted benzothiophenyl, substituted or unsubstituted dibenzothiophenyl, substituted or unsubstituted phenoxazinyl, substituted or unsubstituted phenazinyl, substituted or unsubstituted phenothiazinyl, substituted or unsubstituted thiaoxazinyl, and substituted or unsubstituted thianthrenyl.

In another aspect, the present disclosure provides a display panel including an organic light-emitting device. The organic light-emitting device includes an anode, a cathode arranged opposite to the anode, a capping layer located at a side of the cathode facing away from the anode, and an organic layer located between the anode and the cathode; the organic layer includes an electron transmission layer, a hole transmission layer, and a light-emitting layer, at least one of the capping layer, the electron transmission layer, the hole transmission layer, and the light-emitting layer is made of the nitrogen heterocyclic compound of the present disclosure.

In still another aspect, the present disclosure provides a display apparatus including the display panel above.

DESCRIPTION OF EMBODIMENTS

Figure 1:
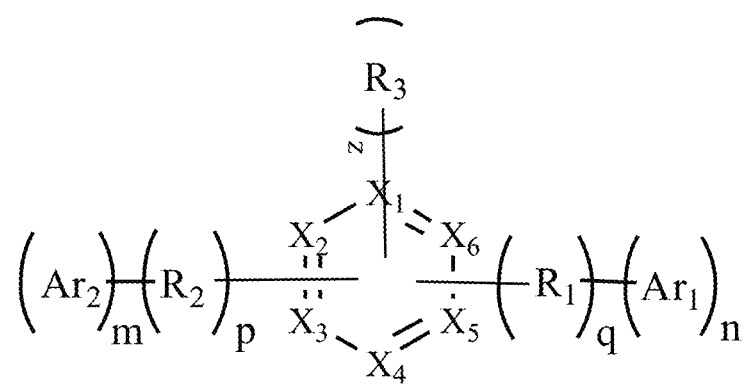
FIG. 1 is a chemical formula of a nitrogen heterocyclic compound according to the present disclosure.

The present disclosure is further described by the following embodiments and comparative examples, which are intended to illustrate the present disclosure, but not to limit the present disclosure. Modifications or equivalent substitutions to the technical solutions of the present disclosure without departing from the scope of the technical solutions should fall within the protection scope of the present disclosure.

In a first aspect, the present disclosure provides a nitrogen heterocyclic compound, having a structure represented by Chemical Formula I:

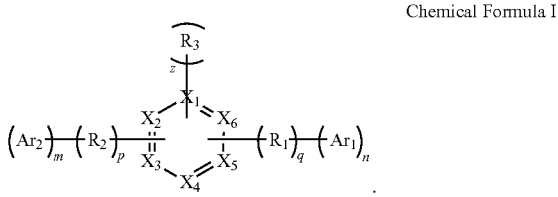

Chemical Formula I

In the Chemical Formula I, z is 1 or 2, m and n are each 1 or 2, and p and q are each 0, 1, or 2.

$X_1$-$X_6$ are each independently nitrogen or carbon, and at least one of $X_1$-$X_6$ is nitrogen.

$R_1$ and $R_2$ are each independently a single bond, C1-C10 linear or branched alkyl, substituted or unsubstituted phenyl, substituted or unsubstituted diphenyl, substituted or unsubstituted terphenyl, substituted or unsubstituted naphthyl, substituted or unsubstituted anthracyl, substituted or unsubstituted acenaphthylenyl, or a substituted or unsubstituted C4-C40 aromatic heterocyclic group selected from a group consisting of pyridyl, thienyl, thiazolyl, thiadiazolyl, furyl, oxazolyl, and oxadiazolyl.

$R_3$ is C1-C10 linear or branched alkyl, substituted or unsubstituted phenyl, substituted or unsubstituted diphenyl, substituted or unsubstituted terphenyl, substituted or unsubstituted naphthyl, substituted or unsubstituted anthracyl, dimethyl fluorenyl, spiro fluorenyl, substituted or unsubstituted acenaphthylenyl, or a substituted or unsubstituted aromatic heterocyclic group selected from a group consisting of pyridyl, thienyl, thiazolyl, thiadiazolyl, furyl, oxazolyl, and oxadiazolyl.

$Ar_1$ and $Ar_2$ are each independently selected from a group consisting of substituted or unsubstituted phenyl, substituted or unsubstituted biphenyl, substituted or unsubstituted naphthyl, substituted or unsubstituted anthracyl, substituted or unsubstituted phenanthryl, substituted or unsubstituted triphenylenyl, substituted or unsubstituted acenaphthylenyl, substituted or unsubstituted pyrenyl, substituted or unsubstituted perylenyl, substituted or unsubstituted fluorenyl, substituted or unsubstituted spirobifluorenyl, substituted or unsubstituted chrysenyl, substituted or unsubstituted benzanthracenyl, substituted or unsubstituted fluoranthenyl, substituted or unsubstituted picenyl, substituted or unsubstituted pyridyl, substituted or unsubstituted pyrimidinyl, substituted or unsubstituted quinolyl, substituted or unsubstituted quinoxalinyl, substituted or unsubstituted phenanthrolinyl, substituted or unsubstituted benzophenanthrolinyl, substituted or unsubstituted furyl, substituted or unsubstituted benzofuranyl, substituted or unsubstituted dibenzofuranyl, substituted or unsubstituted thiophenyl, substituted or unsubstituted benzothiophenyl, substituted or unsubstituted dibenzothiophenyl, substituted or unsubstituted phenoxazinyl, substituted or unsubstituted phenazinyl, substituted or unsubstituted phenothiazinyl, substituted or unsubstituted thiaoxazinyl, and substituted or unsubstituted thianthrenyl.

According to an embodiment of the nitrogen heterocyclic compound of the present disclosure, in the Chemical Formula I, m=n.

According to an embodiment of the nitrogen heterocyclic compound of the present disclosure, in the Chemical Formula I, $R_1$ and $R_2$ are identical According to an embodiment of the nitrogen heterocyclic compound of the present disclosure, in the Chemical Formula I, $Ar_1$ and $Ar_2$ are identical.

According to an embodiment of the nitrogen heterocyclic compound of the present disclosure, in the Chemical Formula I, m=n=1, and z=1; or, m=n=1, and z=2.

According to an embodiment of the nitrogen heterocyclic compound of the present disclosure, in the Chemical Formula I, m=1, n=0, and z=2.

According to an embodiment of the nitrogen heterocyclic compound of the present disclosure, in the Chemical Formula I, only one of $X_1$-$X_6$ is nitrogen.

According to an embodiment of the nitrogen heterocyclic compound of the present disclosure, in the Chemical Formula I, at least two of $X_1$-$X_6$ are nitrogen.

According to an embodiment of the nitrogen heterocyclic compound of the present disclosure, in the Chemical Formula I, three of $X_1$-$X_6$ are nitrogen.

According to an embodiment of the nitrogen heterocyclic compound of the present disclosure, the structure represented by Chemical Formula I is a structure represented by Chemical Formula II, Chemical Formula III, or Chemical Formula IV:

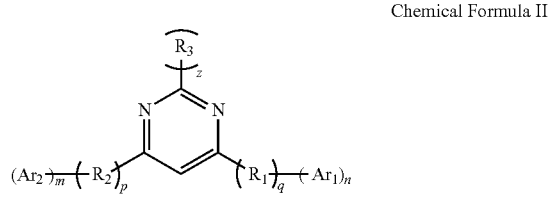

Chemical Formula II

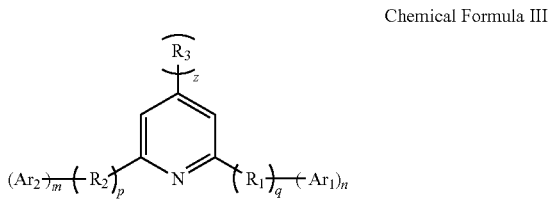

Chemical Formula III

Chemical Formula IV

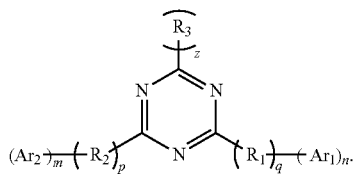

According to an embodiment of the nitrogen heterocyclic compound of the present disclosure, in the Chemical Formula I, $X_2$ and $X_4$ are each nitrogen; or $X_4$ and $X_6$ are each nitrogen.

According to an embodiment of the nitrogen heterocyclic compound of the present disclosure, $R_3$ is selected from a group consisting of phenyl, biphenyl, 4-(4-pyridyl)phenyl, dimethylfluorenyl, spirofluorenyl, naphthyl, anthryl, phenanthryl, triphenylenyl, pyridyl, pyrimidinyl, quinolyl, quinoxalinyl, phenanthrolinyl, and benzophenanthrolinyl.

According to an embodiment of the nitrogen heterocyclic compound of the present disclosure, $Ar_1$ and $Ar_2$ are each independently selected from the following groups:

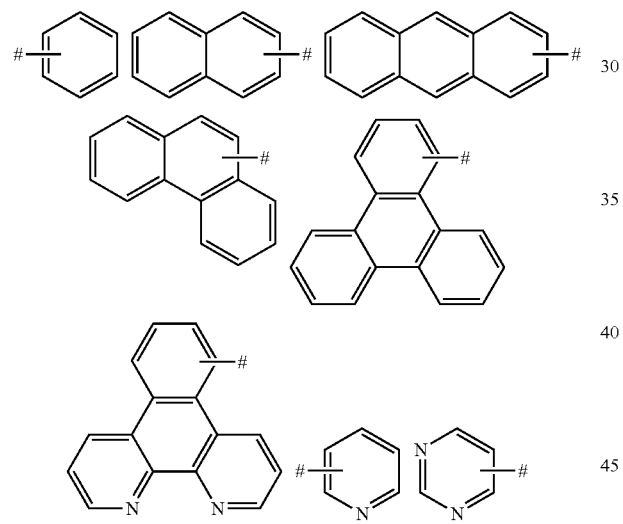

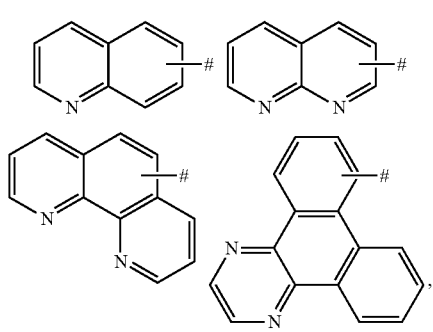

where # represents a bonding position.

According to an embodiment of the nitrogen heterocyclic compound of the present disclosure, the nitrogen heterocyclic compound is any one of the following compounds:

CP1

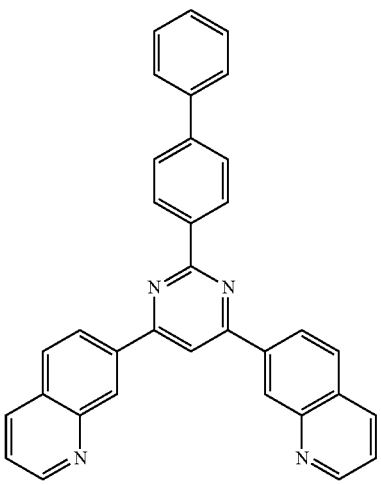

CP2

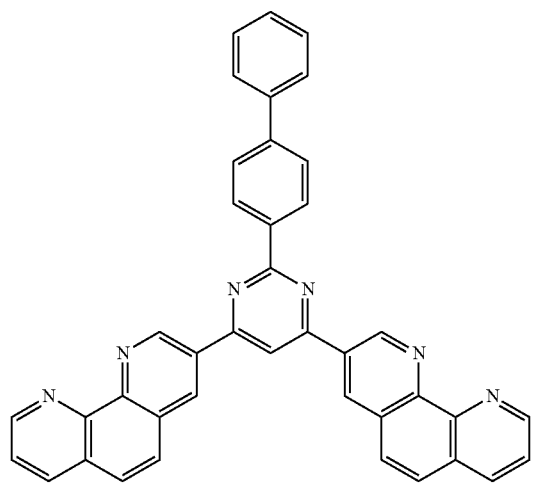

CP3

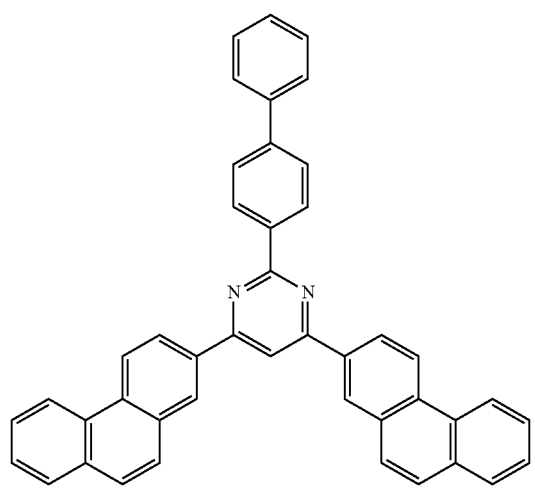

CP4
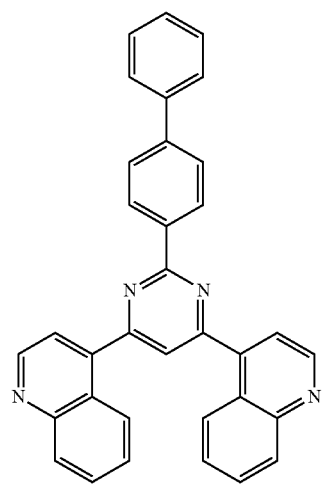
CP5
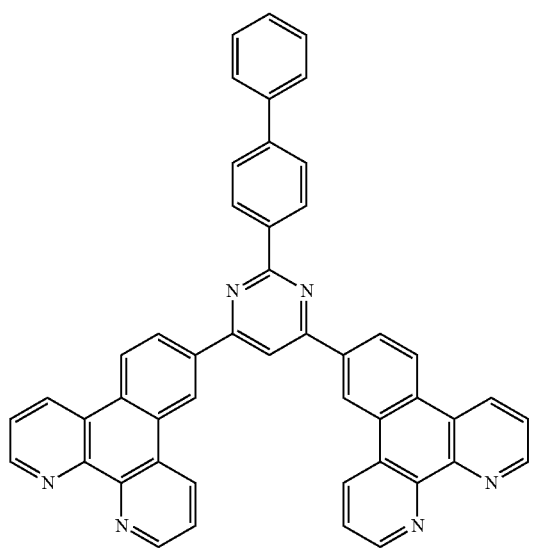
CP6
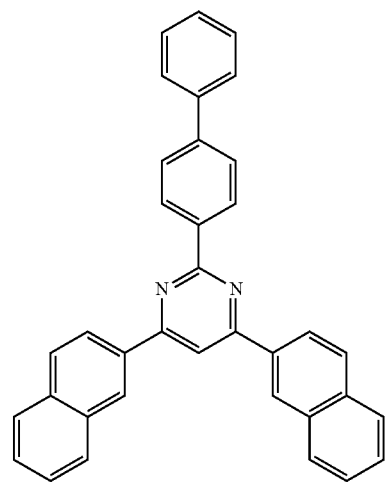
CP7
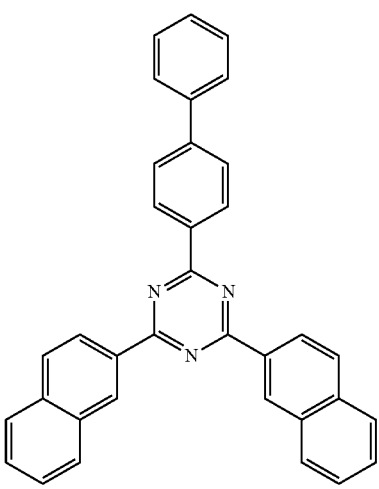
CP8
CP9
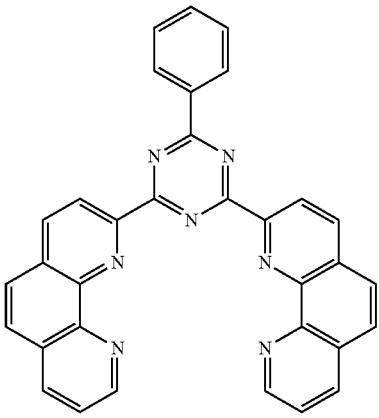

-continued
CP10
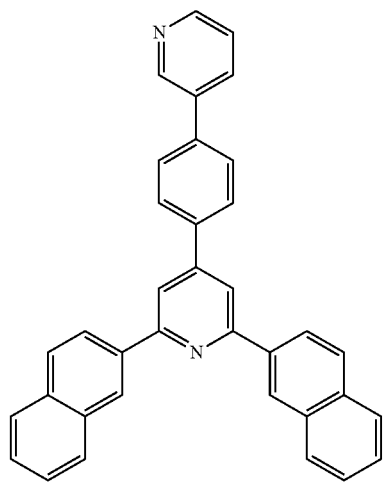
CP11
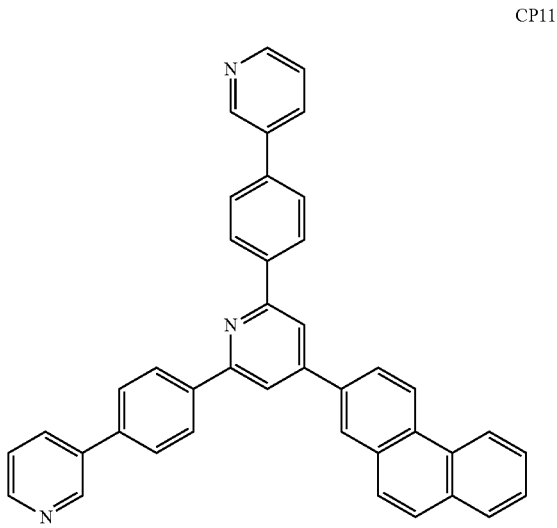
CP12
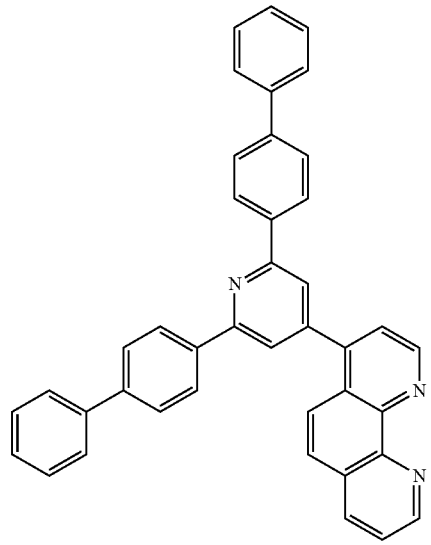
CP13
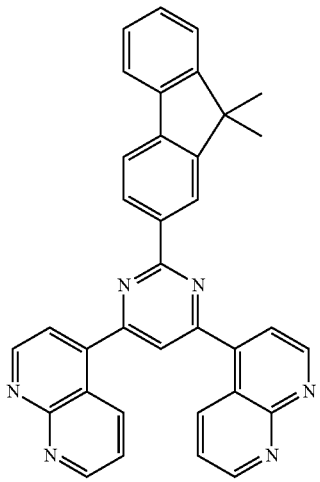
CP14
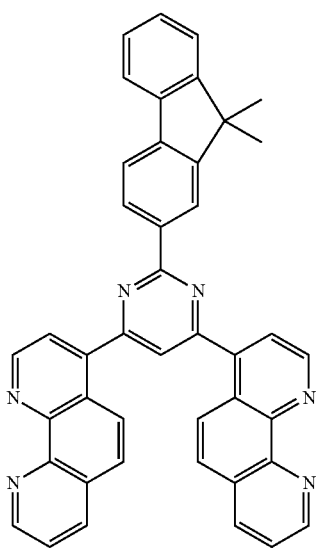
CP15
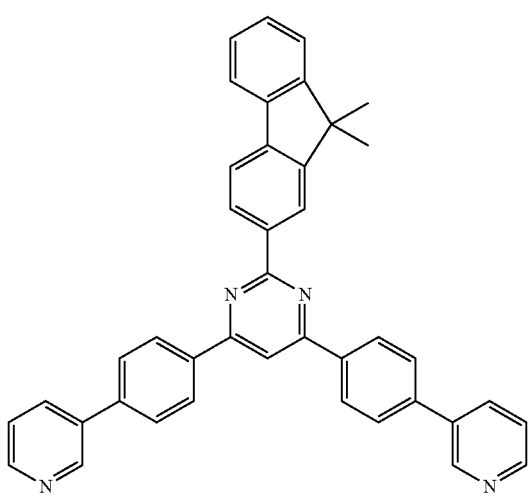

CP16
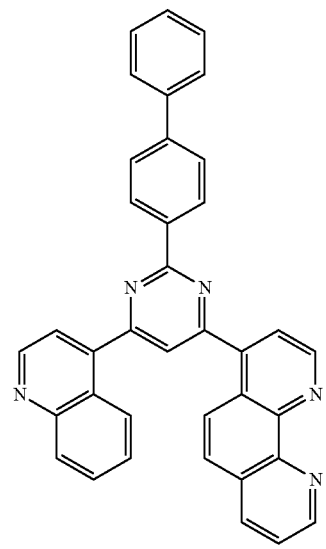
CP17
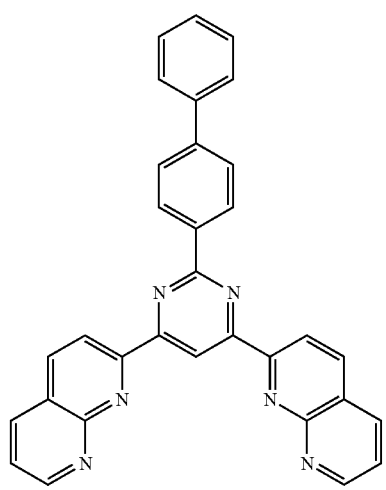
CP18
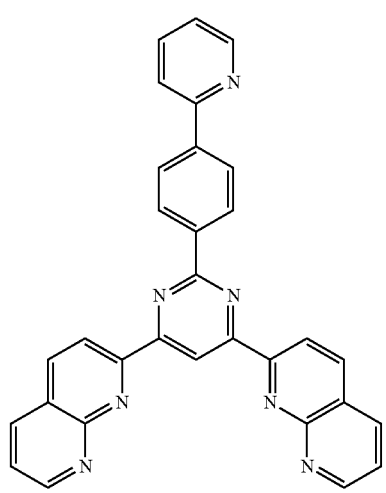
CP19
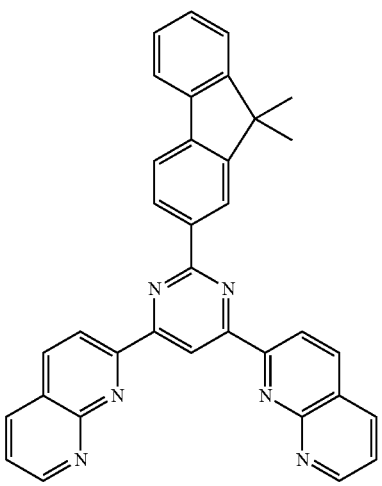
CP20
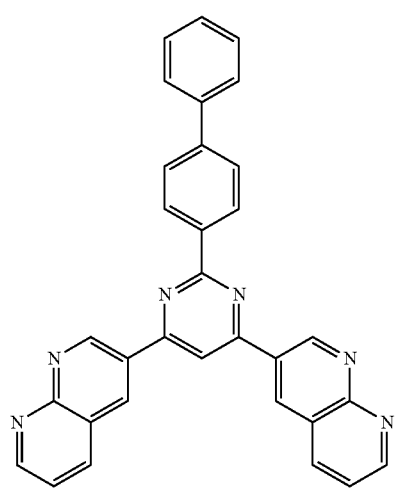
CP21
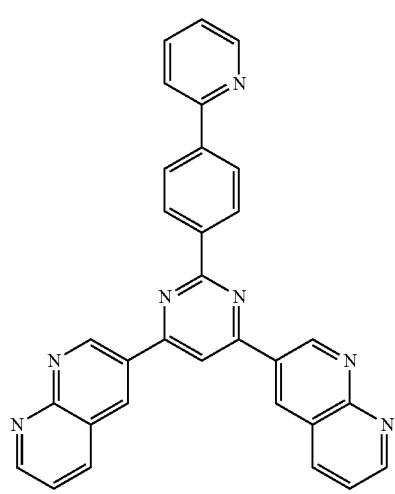

-continued
CP22
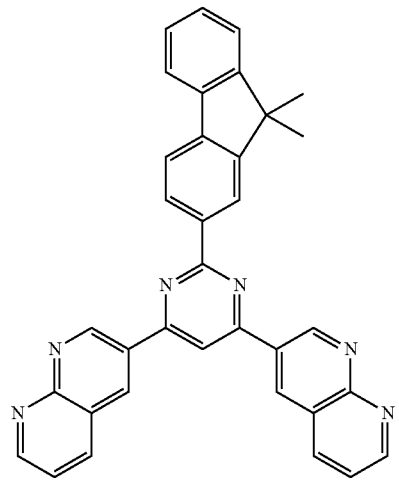
CP25
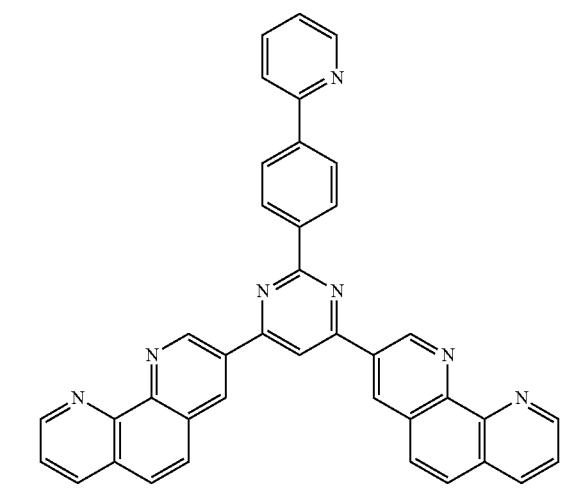
CP23
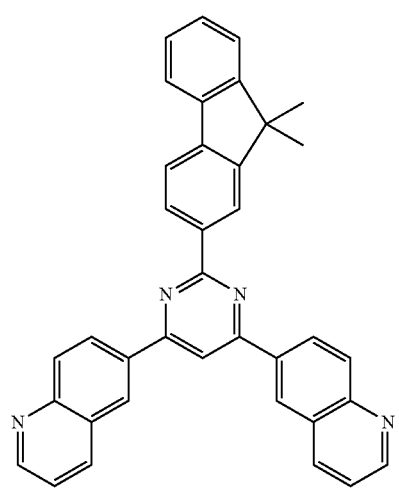
CP26
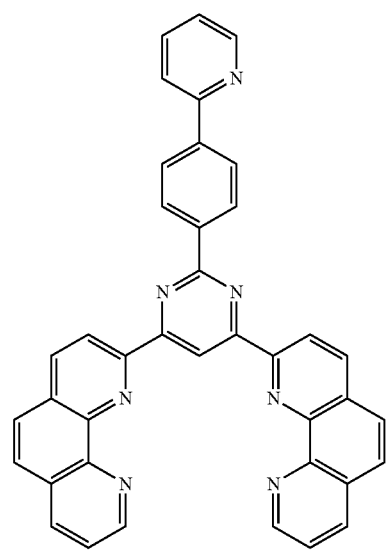
CP24
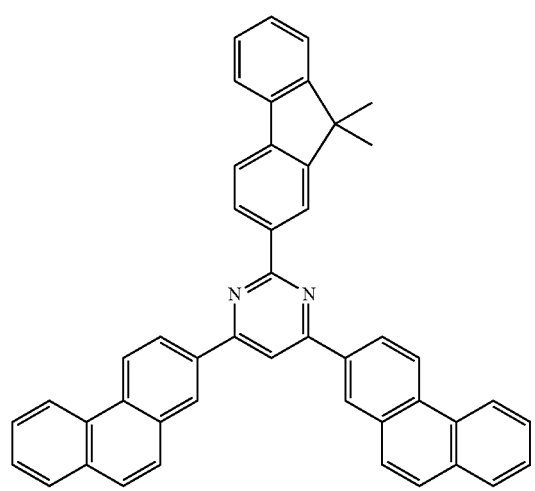
CP27
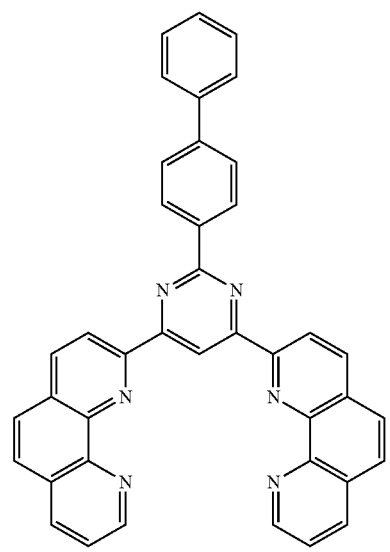

CP28
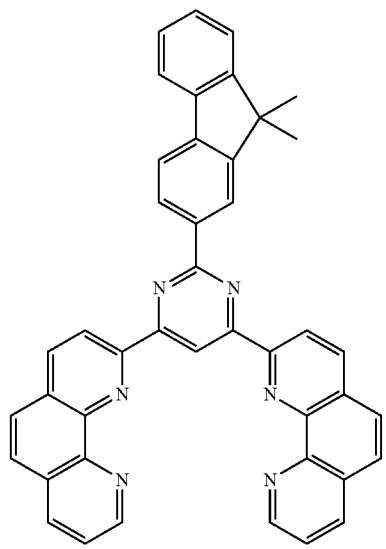
CP29
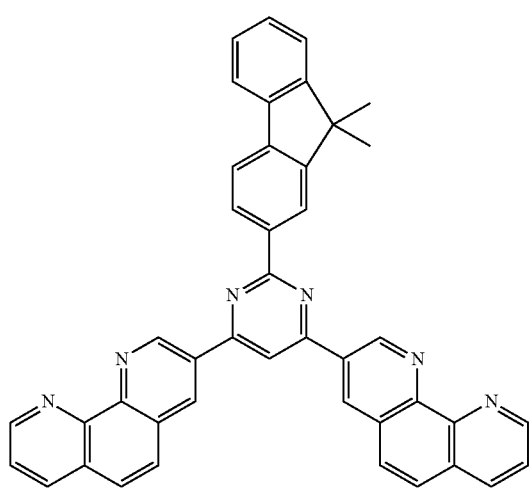
CP30
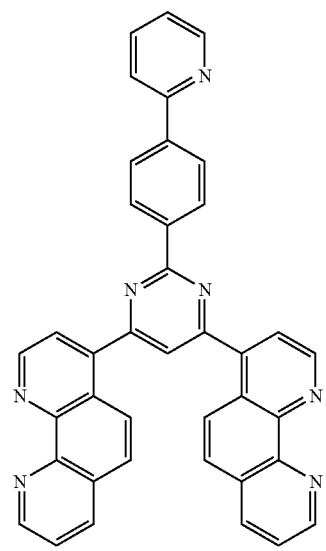
CP31
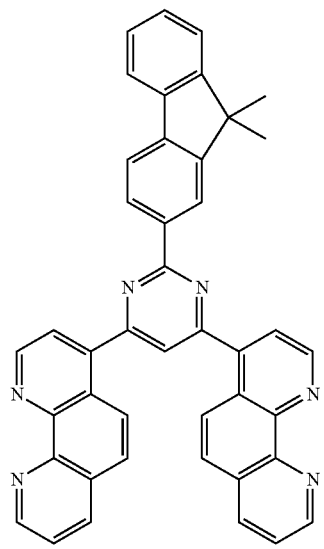
CP32
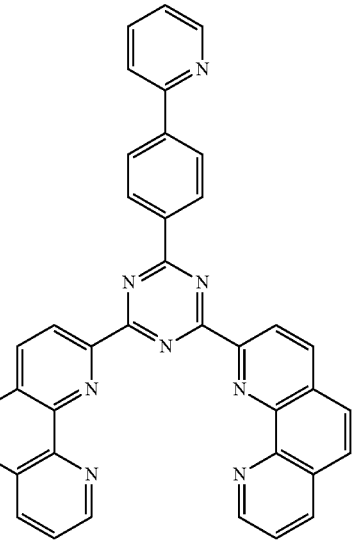
CP33
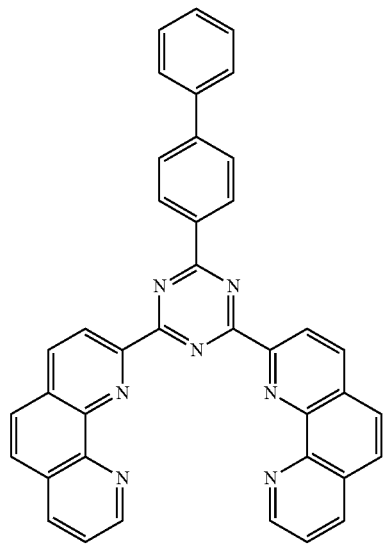

CP34
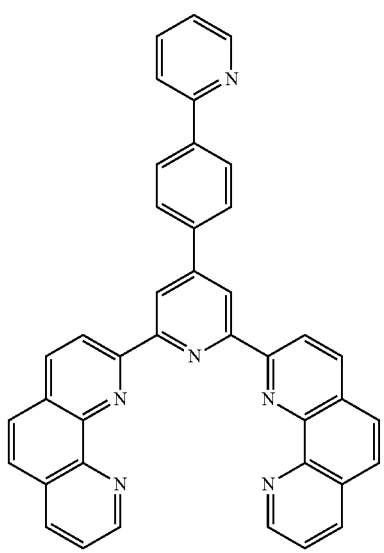
CP35
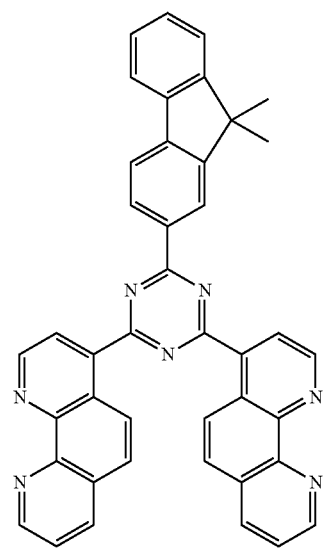
CP36
CP37
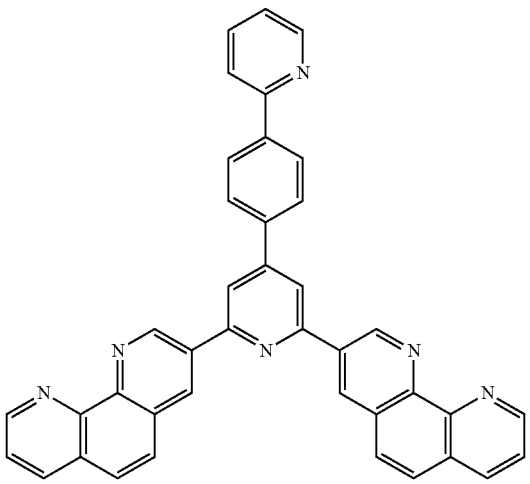
CP38
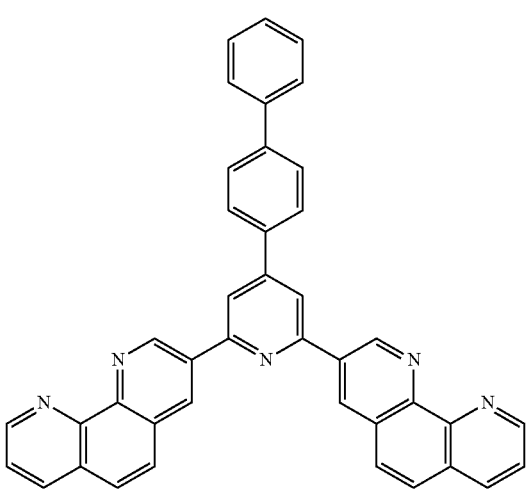
CP39
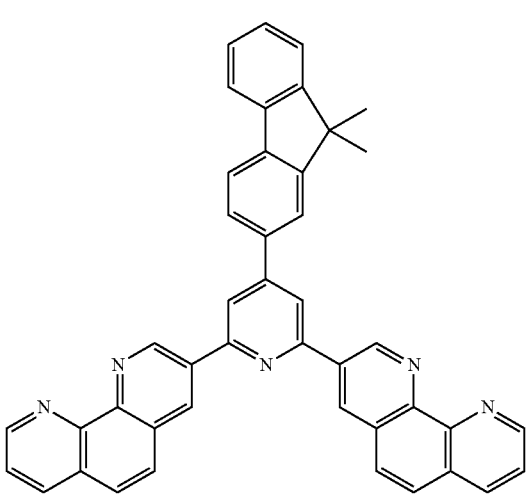

CP40
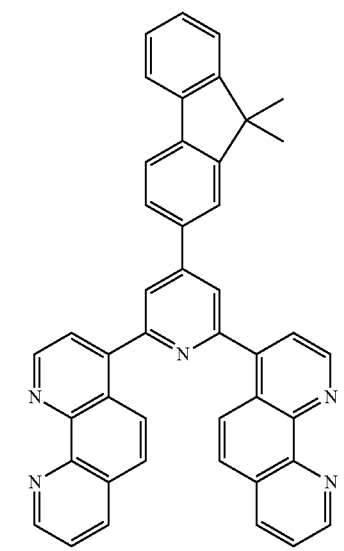
CP41
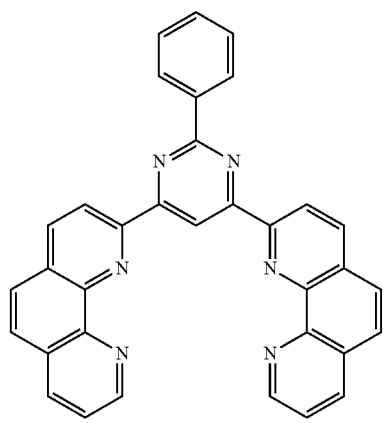
CP42
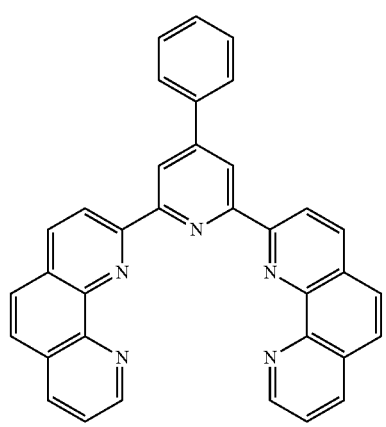
CP43
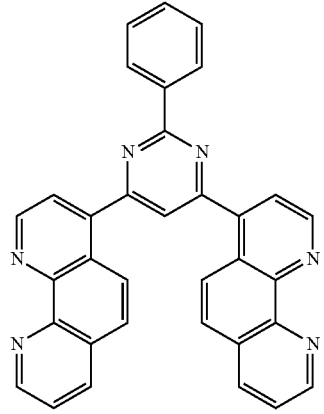
CP44
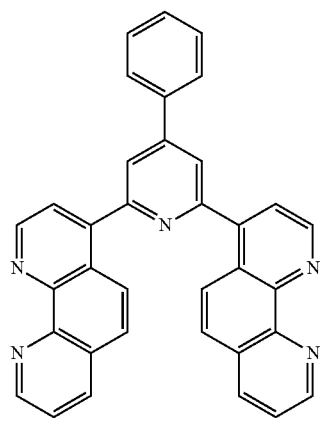
CP45
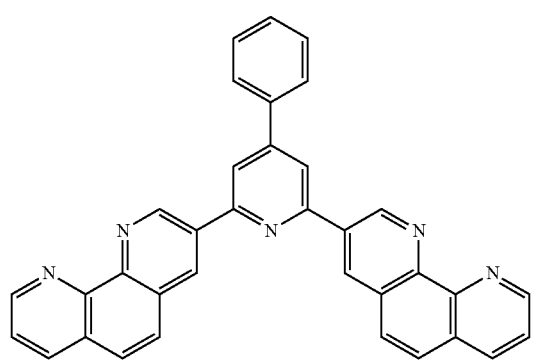
CP46
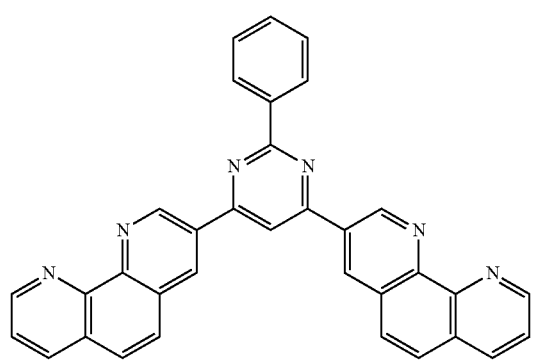

-continued
CP47
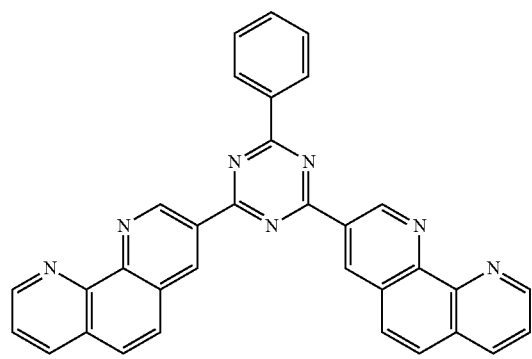
CP48
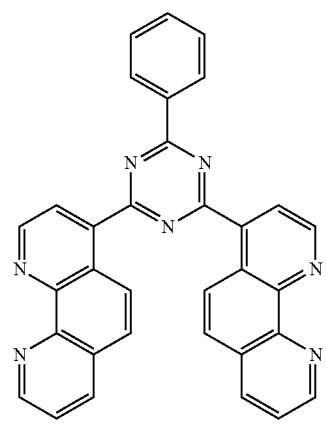
CP49
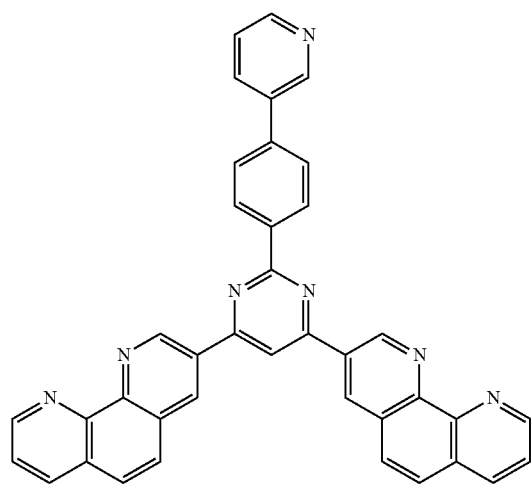
-continued
CP50
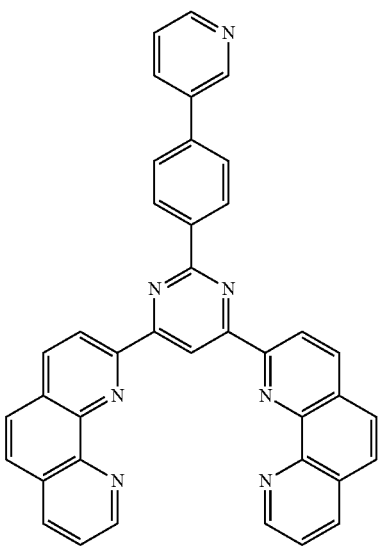
CP51
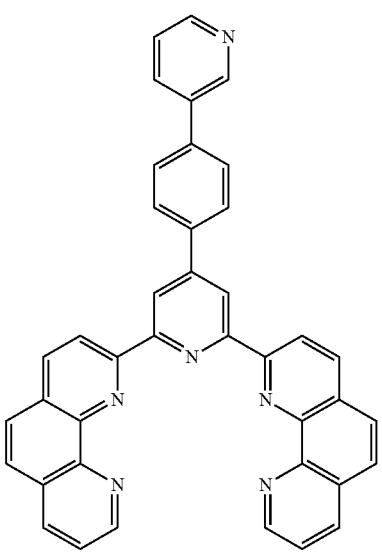
CP52
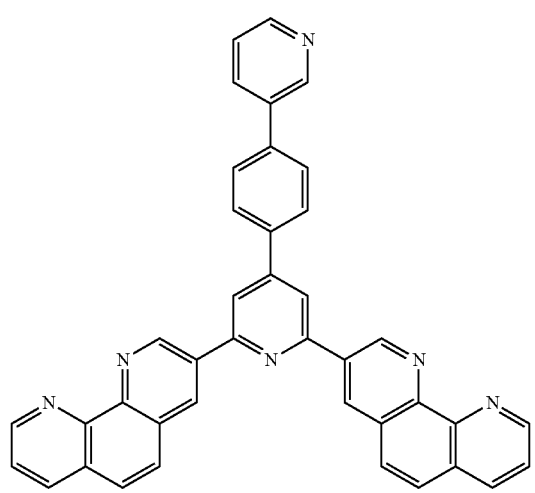

CP53
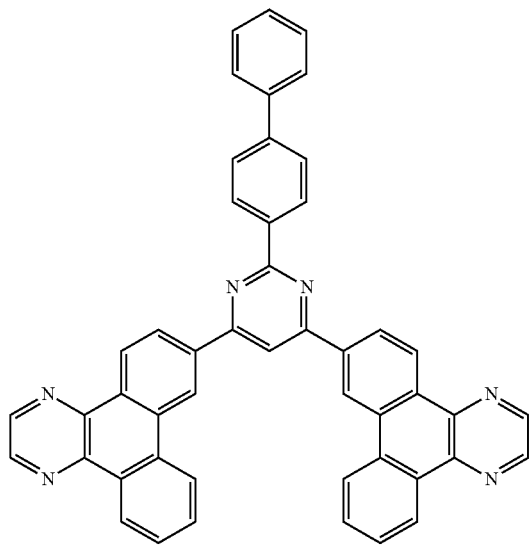
CP54
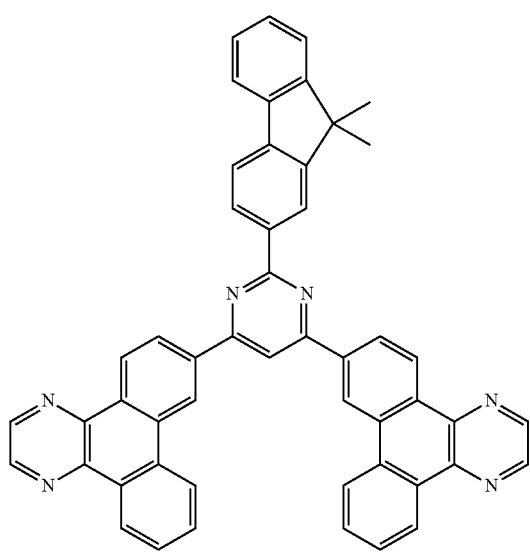
CP55
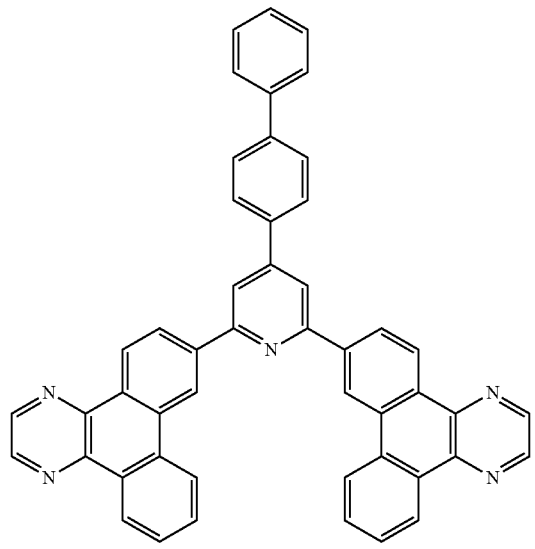
CP56
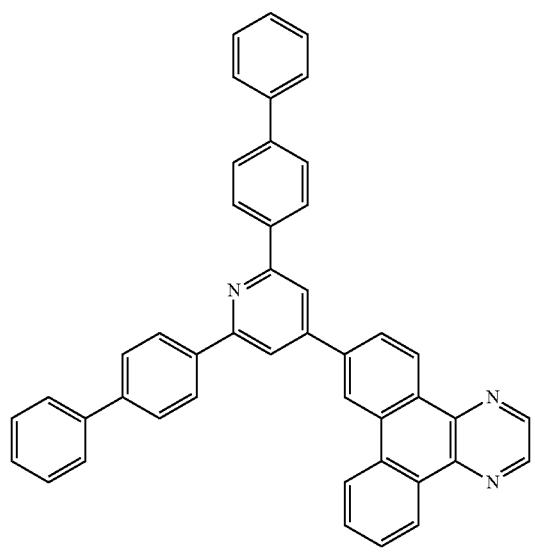
CP57
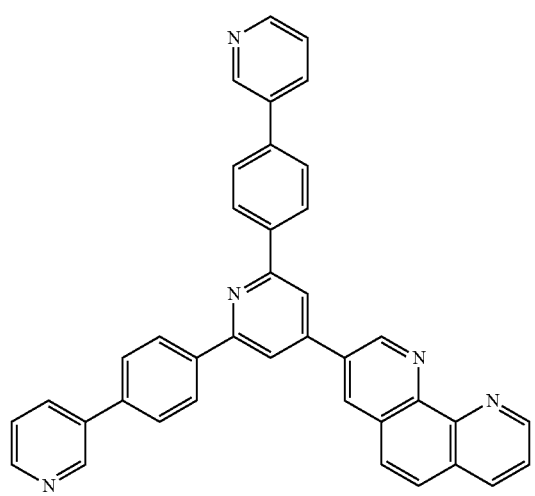

CP58
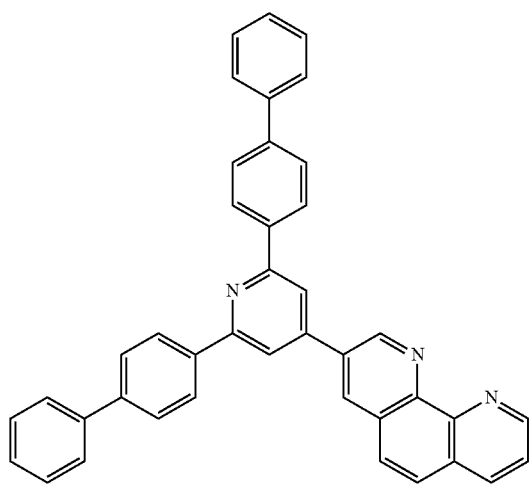
CP59
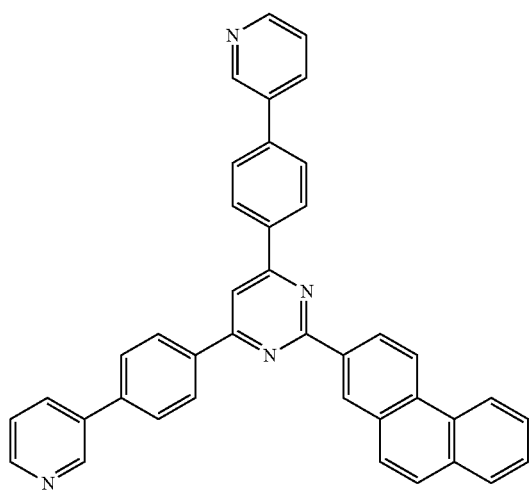
CP60
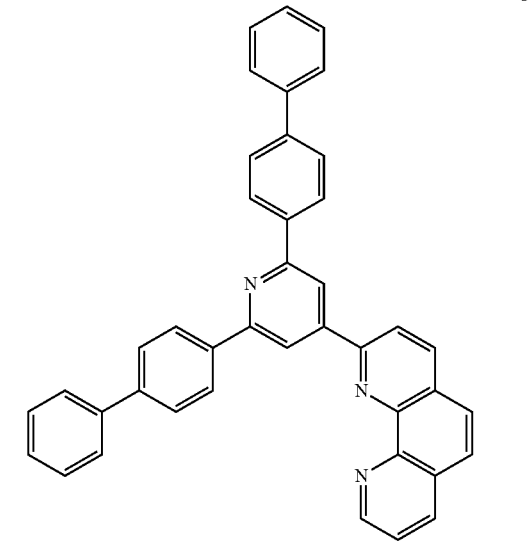
CP61
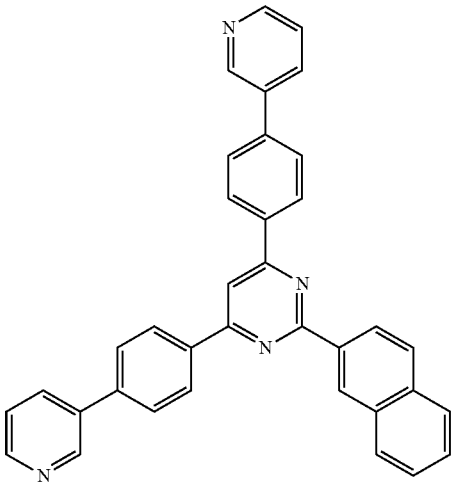
CP62
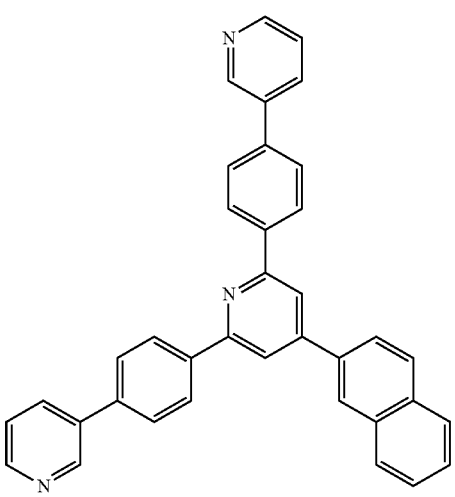
CP63
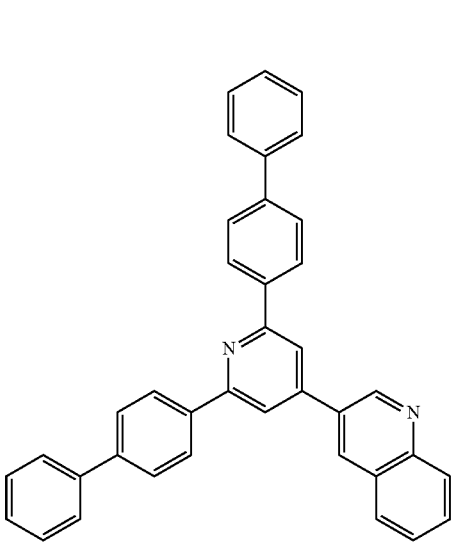

CP64

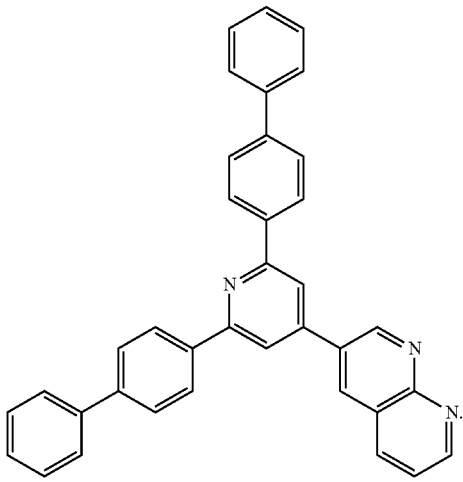

According to an embodiment of the nitrogen heterocyclic compound of the present disclosure, a refractive index n of the nitrogen heterocyclic compound is greater than or equal to 2.0 for visible light having a wavelength between 400 nm and 700 nm.

According to the nitrogen heterocyclic compound of the present disclosure, an extinction coefficient k of the nitrogen heterocyclic compound is smaller than or equal to 0.0 for visible light having a wavelength between 430 nm and 700 nm.

The nitrogen heterocyclic compound of the present disclosure has a relatively high refractive index, and when it is used as a capping layer CPL of an OLED device, EQE of the organic photoelectric device can be effectively improved. In particular, in the blue light region (400-450 nm), the nitrogen heterocyclic compound of the present disclosure has a very small extinction coefficient, and has almost no absorption for blue light, thereby further improving luminous efficiency.

The present disclosure also provides an organic light-emitting device. The organic light-emitting device includes an anode, a cathode arranged opposite to the anode, a capping layer located at a side of the cathode facing away from the anode, and an organic layer located between the anode and the cathode. The organic layer includes an electron transmission layer, a hole transmission layer, and a light-emitting layer. At least one of the capping layer, the electron transmission layer, the hole transmission layer and the light-emitting layer is made of the nitrogen heterocyclic compound described in the present disclosure.

The present disclosure further provides a display panel including the organic light-emitting device of the present disclosure. In the display panel, a stack of the cathode and the cap layer has a transmittance greater than 65% for visible light having a wavelength between 400 nm and 700 nm.

According to an embodiment of the organic light-emitting device of the present disclosure, the organic light-emitting display apparatus further includes one or more layers of a hole injection layer, an electron blocking layer, a hole blocking layer, and an electron injection layer.

In the organic light-emitting device provided by the present disclosure, the anode can be made of a material selected from a group consisting of: metals, such as copper, gold, silver, iron, chromium, nickel, manganese, palladium, platinum, etc., and alloys thereof; metal oxides, such as indium oxide, zinc oxide, indium tin oxide (ITO), indium zinc oxide (IZO), and the like; conductive polymers, such as polyaniline, polypyrrole, poly(3-methylthiophene) and the like. In addition to the above materials and combinations thereof contributing to hole injection, the anode can further include other known material suitable to manufacture the anode.

In the organic light-emitting device of the present disclosure, the materials of the cathode can be selected from a group consisting of: metals, such as aluminum, magnesium, silver, indium, tin, titanium, etc., and alloys thereof; multiple-layer metal materials, such as LiF/Al, $LiO_2$/Al, $BaF_2$/Al, and the like. In addition to the above materials and combinations thereof contributing to electron injection, the cathode can further include other known material suitable to manufacture the cathode.

In the present disclosure, the organic light-emitting device can be manufactured by forming an anode on a transparent or opaque smooth substrate, forming a thin organic layer on the anode, and further forming a cathode on the thin organic layer. The thin organic layer can be formed by a known film forming method such as vapor deposition, sputtering, spin coating, dipping, ion plating, and the like. Finally, an organic optical capping layer (CPL) was prepared on the cathode. The material of the CPL is the nitrogen heterocyclic compound described in the present disclosure. The CPL can be prepared by vapor evaporation or a solution method. The solution method includes an ink-jet printing method, spin coating, blade coating, screen printing, roll-to-roll printing, and the like.

The nitrogen heterocyclic compound of the present disclosure can be not only used as a material for the capping layer CPL of the organic light-emitting device but also used as materials for an auxiliary electron transmission layer and for the light-emitting layer.

Synthesis of intermediates for preparation of exemplary nitrogen heterocyclic compounds is described below.

A synthetic route of Intermediate M1 is as follows:

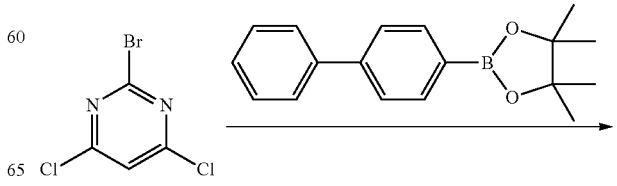

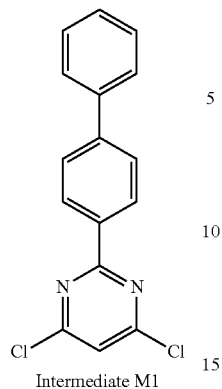

Intermediate M1

In nitrogen atmosphere, raw materials of 2-bromo-4,6-dichloropyrimidine (0.012 mol), biphenyl borate (0.012 mol) and palladium acetate (0.0003 mol) were sequentially added to 150 ml DMF in a 250 ml three-necked flask, mixed and stirred. After a solution of $K_3PO_4$ (0.045 mol) in water was added, the mixture was refluxed for 10 h at a temperature of 130° C., and then naturally cooled to room temperature. After completion of the reaction, 100 mL deionized water was added, and then a few droplets of 2M HCl were added. The reacted mixture was extracted with dichloromethane, and an organic phase was collected and dried by anhydrous $Na_2SO_4$. The dried solution was filtered, and the solvent was removed using a rotary evaporator to obtain a crude product. The obtained crude product was purified through silica gel column chromatography to obtain the Intermediate M1.

Elemental analysis of the Intermediate M1 (Molecular Formula $C_{16}H_{10}Cl_2N_2$): theoretical value: C, 63.81; H, 3.35; Cl, 23.54; N, 9.30; test value: C, 63.83; H, 3.36; Cl, 23.53; N, 9.28. The ESI-MS (m/z) (M+) was obtained by liquid chromatography-mass spectrometry: theoretical value: 300.02, and test value: 300.025.

A synthetic route of Intermediate M4 is as follows:

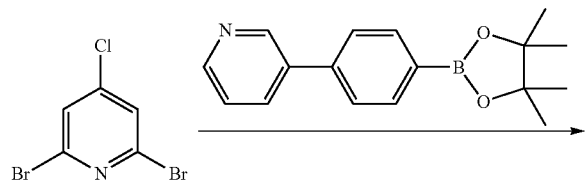

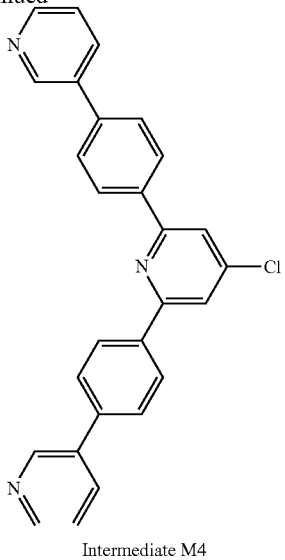

Intermediate M4

In nitrogen atmosphere, raw materials of 2-bromo-4,6-dichloropyrimidine (0.012 mol), 4-pyridine-phenylborate (0.025 mol) and palladium acetate (0.0003 mol) were sequentially added to 150 ml DMF in a 250 ml three-necked flask, mixed and stirred. After a solution of $K_3PO_4$ (0.045 mol) in water was added, the mixture was refluxed for 10 h at a temperature of 130° C., and then naturally cooled to room temperature. After completion of the reaction, 100 mL deionized water was added, and then a few droplets of 2M HCl were added. The reacted mixture was extracted with dichloromethane, and an organic phase was collected and dried by anhydrous $Na_2SO_4$. The dried solution was filtered, and the solvent was removed using a rotary evaporator to obtain a crude product. The obtained crude product was purified through silica gel column chromatography to obtain the Intermediate M4.

Elemental analysis of the Intermediate M4 (Molecular Formula $C_{27}H_{18}ClN_3$): theoretical value: C, 77.23; H, 4.32; Cl, 8.44; N, 10.01; test value: C, 77.23; H, 4.33; Cl, 8.42; N, 10.02. The ESI-MS (m/z) (M+) was obtained by liquid chromatography-mass spectrometry: theoretical value: 419.12, and test value: 419.24.

Main raw materials for synthesis of Intermediates M1, M2, M3, and M4 are listed in Table 1. Methods for synthesis of Intermediate M1 to Intermediate M4 were consistent.

TABLE 1

| Raw material 1 | Raw material 2 | Intermediate |
|---|---|---|
| (2-bromo-4,6-dichloropyrimidine) | (4-biphenyl boronic acid pinacol ester) | Intermediate M1 |

TABLE 1-continued

| Raw material 1 | Raw material 2 | Intermediate |
|---|---|---|
| | | Intermediate M2 |
| | | Intermediate M3 |
| | | Intermediate M4 |

Another aspect of the present disclosure provides methods for preparing several exemplary nitrogen heterocyclic compounds, which are described in exemplary Examples 1-6 below.

Example 1

Synthesis of Compound CP2

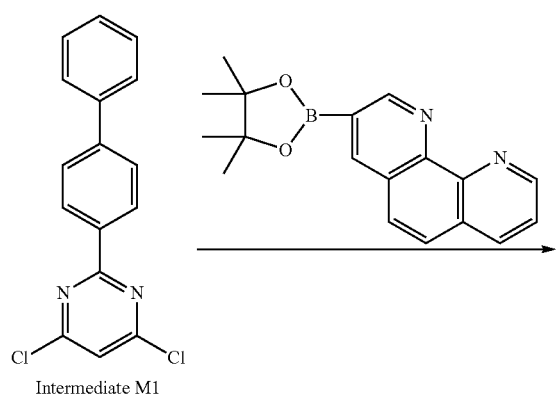

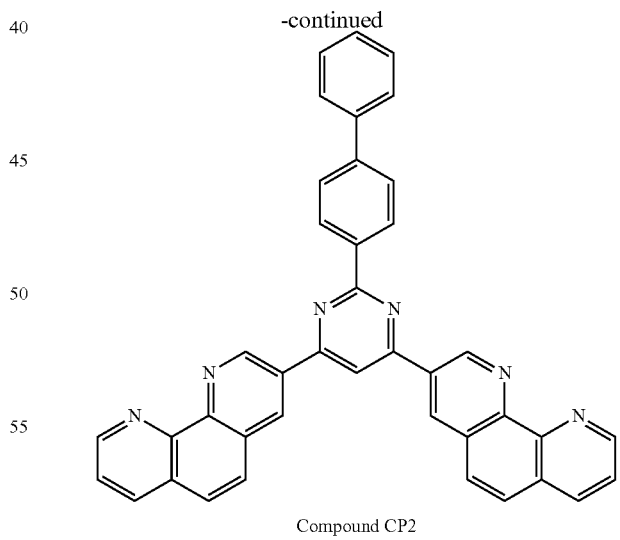

In nitrogen atmosphere, raw materials of the Intermediate M1 (0.012 mol), 3-o-phenanthrolinyl borate (0.025 mol) and palladium acetate (0.0003 mol) were sequentially added to 150 ml DMF in a 250 ml three-necked flask, mixed and stirred. After a solution of $K_3PO_4$ (0.045 mol) in water was added, the mixture was refluxed for 10 h at a temperature of 130° C., and then naturally cooled to room temperature.

After completion of the reaction, 100 mL deionized water was added, and a few droplets of 2M HCl were added. The reacted mixture was then extracted with dichloromethane, and an organic phase was collected and dried by anhydrous Na$_2$SO$_4$. The dried solution was filtered, and the solvent was removed using a rotary evaporator to obtain a crude product. The obtained crude product was purified through silica gel column chromatography to obtain the Compound CP2.

Elemental analysis of the Compound CP2 (Molecular Formula C$_{40}$H$_{24}$N$_6$): theoretical value: C, 81.61; H, 4.11; N, 14.28; test value: C, 81.63; H, 4.11; N, 14.26. The ESI-MS (m/z) (M+) was obtained by liquid chromatography-mass spectrometry: theoretical value: 588.21, and test value: 588.43.

Example 2

Synthesis of Compound CP4:

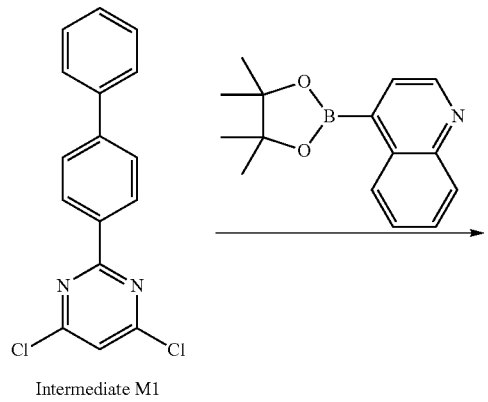

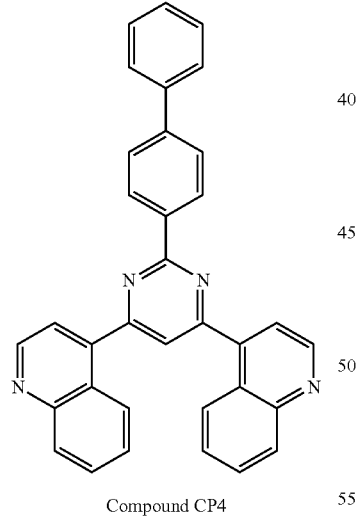

Compound CP4

In nitrogen atmosphere, raw materials of the Intermediate M1 (0.012 mol), 4-quinolinyl borate (0.025 mol) and palladium acetate (0.0003 mol) were sequentially added to 150 ml DMF in a 250 ml three-necked flask, mixed and stirred. After a solution of K$_3$PO$_4$ (0.045 mol) in water was added, the mixture was refluxed for 10 h at a temperature of 130° C., and then naturally cooled to room temperature. After completion of the reaction, 100 mL deionized water was added, and then a few droplets of 2M HCl were added. The reacted mixture was extracted with dichloromethane, and an organic phase was collected and dried by anhydrous Na$_2$SO$_4$. The dried solution was filtered, and the solvent was removed using a rotary evaporator to obtain a crude product. The obtained crude product was purified through silica gel column chromatography to obtain the Compound CP4.

Elemental analysis of the Compound CP4 (Molecular Formula C$_{34}$H$_{22}$N$_4$): theoretical value: C, 83.93; H, 4.56; N, 11.51; test value: C, 83.95; H, 4.54; N, 11.51. The ESI-MS (m/z) (M+) was obtained by liquid chromatography-mass spectrometry: theoretical value: 486.18, and test value: 486.30.

Example 3

Synthesis of Compound CP8:

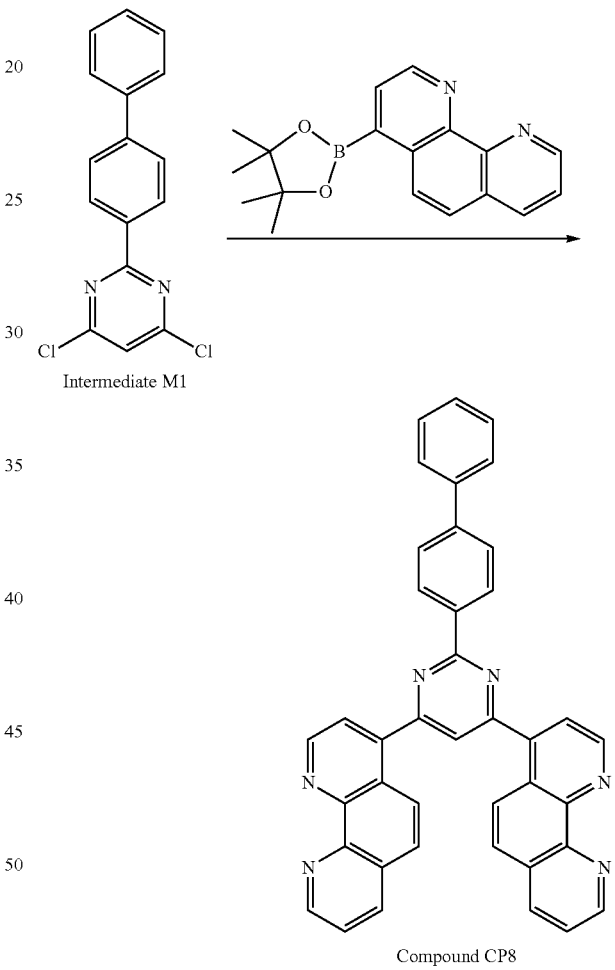

Compound CP8

In nitrogen atmosphere, raw materials of the Intermediate M1 (0.012 mol), 4-o-phenanthrolinyl borate (0.025 mol) and palladium acetate (0.0003 mol) were sequentially added to 150 ml DMF in a 250 ml three-necked flask, mixed and stirred. After a solution of K$_3$PO$_4$ (0.045 mol) in water was added, the mixture was refluxed for 10 h at a temperature of 130° C., and then naturally cooled to room temperature. After completion of the reaction, 100 mL deionized water was added, and a few droplets of 2M HCl were added. The reacted mixture was then extracted with dichloromethane, and an organic phase was collected and dried by anhydrous Na$_2$SO$_4$. The dried solution was filtered, and the solvent was removed using a rotary evaporator to obtain a crude product. The obtained crude product was purified through silica gel column chromatography to obtain the Compound CP8.

Elemental analysis of the Compound CP8 (Molecular Formula $C_{40}H_{24}N_6$): theoretical value: C, 81.61; H, 4.11; N, 14.28; test value: C, 81.64; H, 4.10; N, 14.26. The ESI-MS (m/z) (M+) was obtained by liquid chromatography-mass spectrometry: theoretical value: 588.21, and test value: 588.42.

Example 4

Synthesis of Compound CP11:

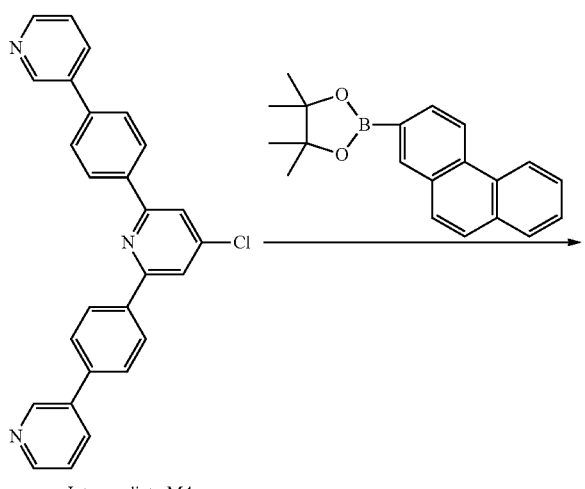

Intermediate M4

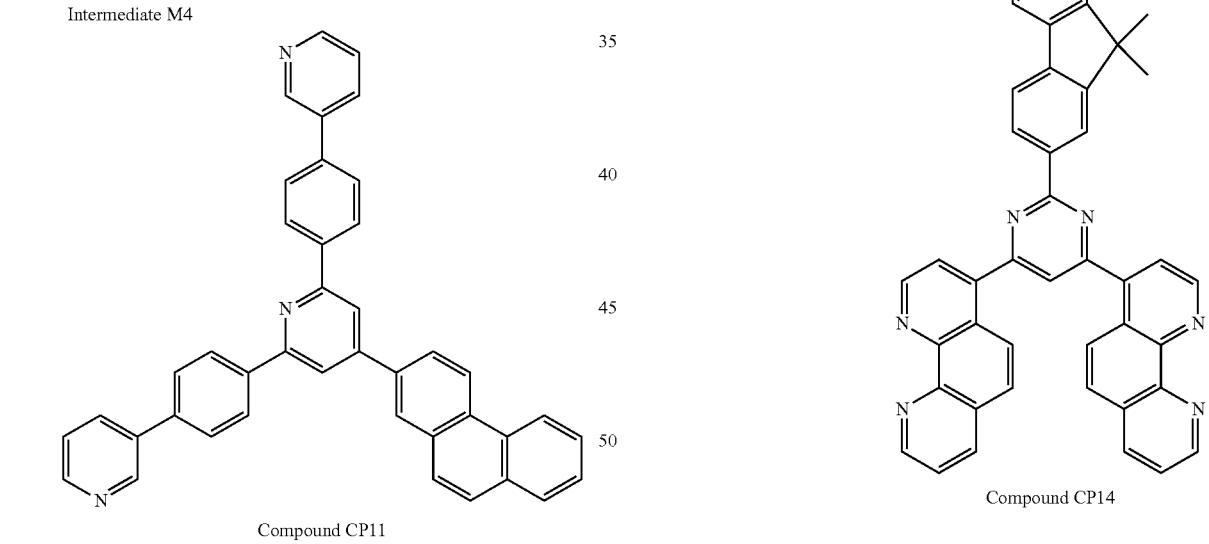

Compound CP11

In nitrogen atmosphere, raw materials of the Intermediate M4 (0.012 mol), 1-phenanthryl borate (0.012 mol) and palladium acetate (0.0003 mol) were sequentially added to 150 ml DMF in a 250 ml three-necked flask, mixed and stirred. After a solution of $K_3PO_4$ (0.045 mol) in water was added, the mixture was refluxed for 10 h at a temperature of 130° C., and then naturally cooled to room temperature. After completion of the reaction, 100 mL deionized water was added, and a few droplets of 2M HCl were added. The reacted mixture was then extracted with dichloromethane, and an organic phase was collected and dried by anhydrous $Na_2SO_4$. The dried solution was filtered, and the solvent was removed using a rotary evaporator to obtain a crude product. The obtained crude product was purified through silica gel column chromatography to obtain the Compound CP11.

Elemental analysis of the Compound CP11 (Molecular Formula $C_{41}H_{27}N_3$): theoretical value: C, 87.67; H, 4.85; N, 7.48; test value: C, 87.69; H, 4.84; N, 7.47. The ESI-MS (m/z) (M+) was obtained by liquid chromatography-mass spectrometry: theoretical value: 561.22, and test value: 561.56.

Example 5

Synthesis of Compound CP14:

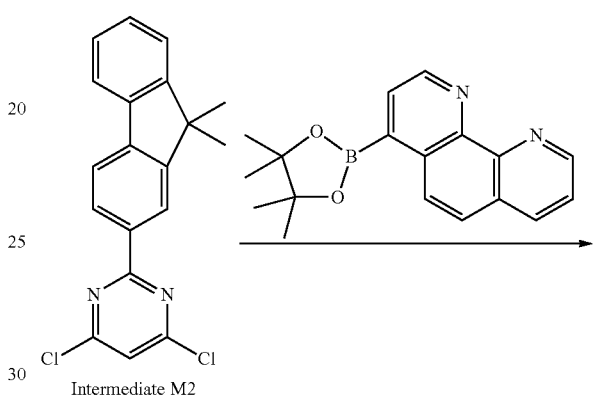

Intermediate M2

Compound CP14

In nitrogen atmosphere, raw materials of the Intermediate M2 (0.012 mol), 4-o-phenanthrolinyl borate (0.025 mol) and palladium acetate (0.0003 mol) were sequentially added to 150 ml DMF in a 250 ml three-necked flask, mixed and stirred. After a solution of $K_3PO_4$ (0.045 mol) in water was added, the mixture was refluxed for 10 h at a temperature of 130° C., and then naturally cooled to room temperature. After completion of the reaction, 100 mL deionized water was added, and then a few droplets of 2M HCl were added. The reacted mixture was then extracted with dichloromethane, and an organic phase was collected and dried by anhydrous $Na_2SO_4$. The dried solution was filtered, and the solvent was removed using a rotary evaporator to obtain a crude product. The obtained crude product was purified through silica gel column chromatography to obtain the Compound CP14.

Elemental analysis of the Compound CP11 ($C_{43}H_{28}N_6$): theoretical value: C, 82.14; H, 4.49; N, 13.37; test value: C, 82.17; H, 4.48; N, 13.35. The ESI-MS (m/z) (M+) was obtained by liquid chromatography-mass spectrometry: theoretical value: 628.24, and test value: 628.29.

Example 6

Synthesis of Compound CP42:

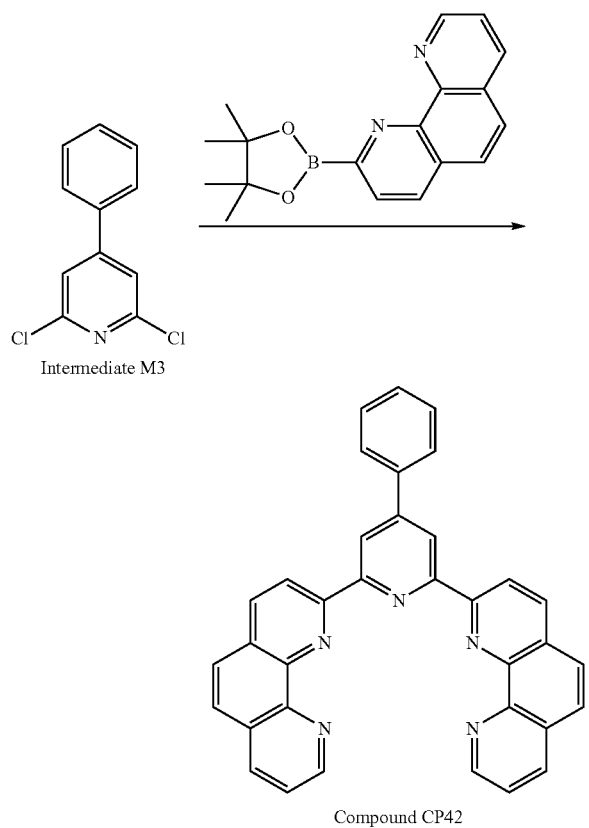

In nitrogen atmosphere, raw materials of the Intermediate M3 (0.012 mol), 2-o-phenanthrolinyl borate (0.025 mol) and palladium acetate (0.0003 mol) were sequentially added to 150 ml DMF in a 250 ml three-necked flask, mixed and stirred. After a solution of $K_3PO_4$ (0.045 mol) in water was added, the mixture was refluxed for 10 h at a temperature of 130° C., and then naturally cooled to room temperature. After completion of the reaction, 100 mL deionized water was added, and then a few droplets of 2M HCl were added. The reacted mixture was then extracted with dichloromethane, and an organic phase was collected and dried by anhydrous $Na_2SO_4$. The dried solution was filtered, and the solvent was removed using a rotary evaporator to obtain a crude product. The obtained crude product was purified through silica gel column chromatography to obtain the Compound CP42.

Elemental analysis of the Compound CP42 ($C_{35}H_{21}N_5$): theoretical value: C, 82.17; H, 4.14; N, 13.69; test value: C, 82.16; H, 4.13; N, 13.71. The ESI-MS (m/z) (M+) was obtained by liquid chromatography-mass spectrometry: theoretical value: 511.18, and test value: 511.50.

Test results of the thermal properties and refractive indexes of the nitrogen heterocyclic compounds according to the present disclosure are listed in Table 2. In Table 2, comparisons were made by using compounds CBP, Alq3, and TPBI.

TABLE 2 test results of thermal performance and refractive index

| compound | Tg (° C.) | refractive index | | |
|---|---|---|---|---|
| | | n@450 | n@530 | n@620 |
| CP1 | 154 | 2.38 | 2.17 | 2.06 |
| CP2 | 153 | 2.45 | 2.23 | 2.11 |
| CP4 | 160 | 2.43 | 2.22 | 2.09 |
| CP8 | 157 | 2.52 | 2.24 | 2.13 |
| CP11 | 162 | 2.49 | 2.20 | 2.08 |
| CP14 | 161 | 2.50 | 2.23 | 2.10 |
| CP20 | 158 | 2.46 | 2.20 | 2.08 |
| CP21 | 154 | 2.37 | 2.19 | 2.02 |
| CP30 | 156 | 2.41 | 2.19 | 2.07 |
| CP35 | 160 | 2.53 | 2.24 | 2.12 |
| CP42 | 158 | 2.47 | 2.23 | 2.11 |
| CP62 | 155 | 2.49 | 2.24 | 2.12 |
| CBP | 108 | 1.87 | 1.81 | 1.78 |
| Alq3 | 149 | 1.78 | 1.75 | 1.73 |
| TPBi | 121 | 1.80 | 1.76 | 1.73 |

* Taking n@450 as an example, n@450 means the refractive index of the nitrogen heterocyclic compound for light having a wavelength of 450 nm.

As can be seen from the above Table 2, for visible light having a wavelength of 450-620 nm, the refractive indexes of all of the nitrogen heterocyclic compounds of the present disclosure are greater than 2.0, which can satisfy the refractive index requirement to the CPL of the light-emitting device, thereby achieving higher luminous efficiency. Further, all of the nitrogen heterocyclic compounds of the present disclosure have a glass transition temperature Tg higher than 150° C., and therefore, when these nitrogen heterocyclic compounds are applied to light-emitting devices, the light-emitting devices can have higher stability.

Figure 3:
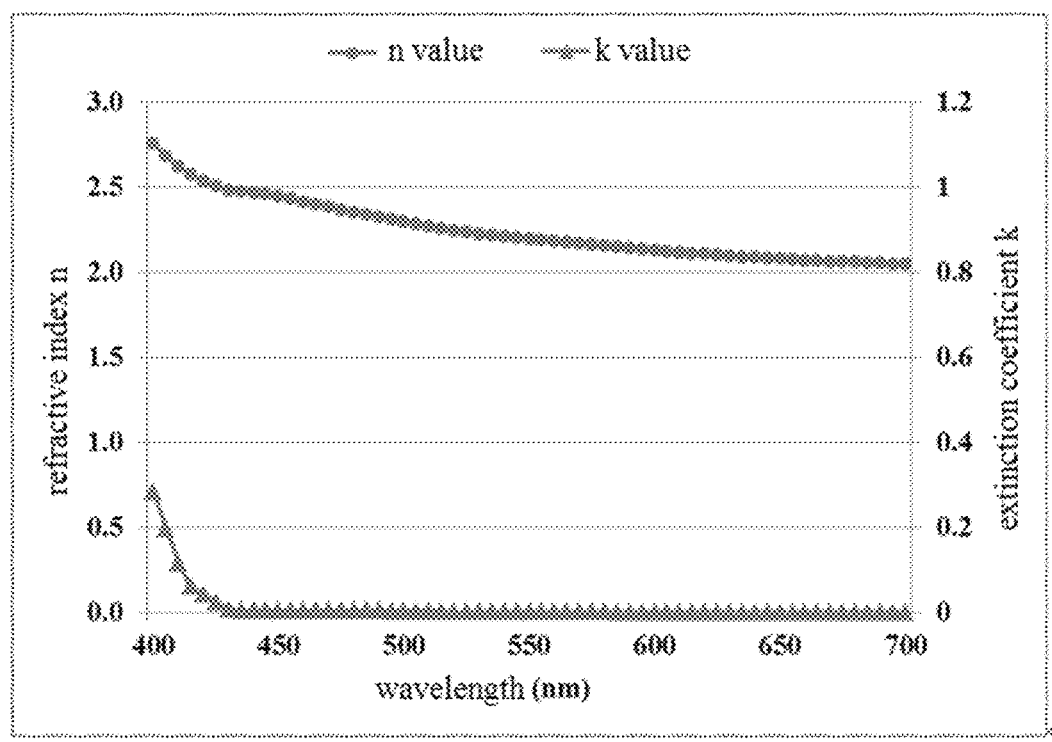
FIG. 3 is a graph showing refractive index and extinction coefficient of compound CP2 according to an embodiment of the present disclosure.
Figure 4:
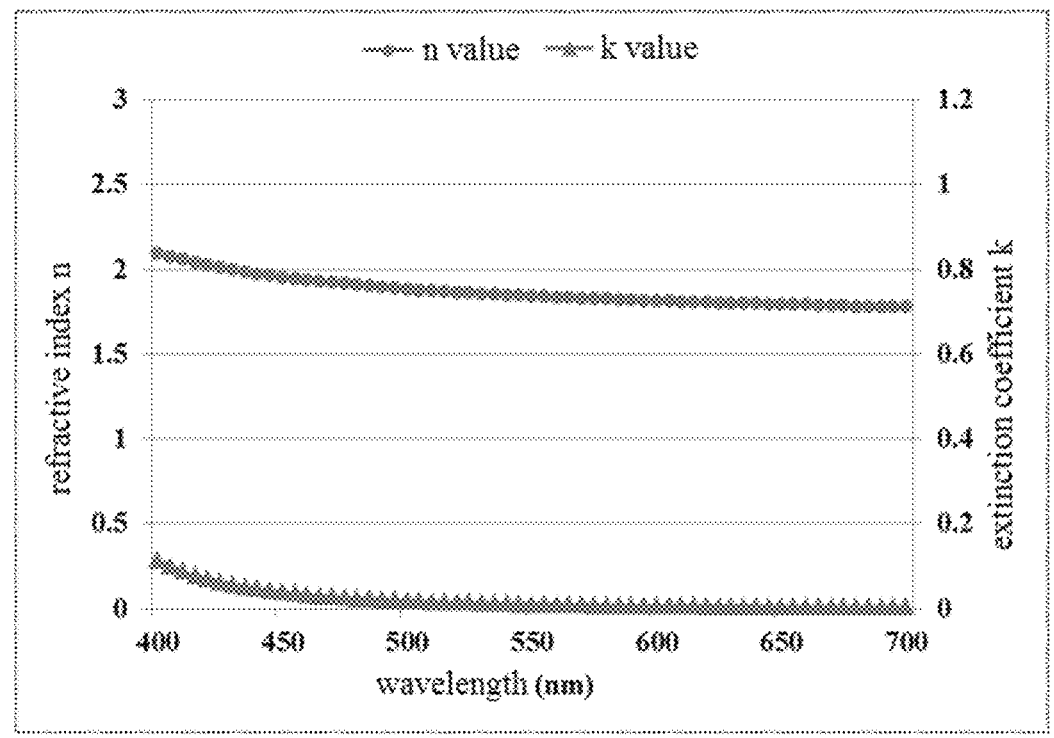
FIG. 4 is a graph showing refractive index and extinction coefficient of compound CBP in a comparative example.

FIG. 3 is a graph showing refractive index and extinction coefficient of CP2 according to an embodiment of the present disclosure; and FIG. 4 is a graph showing refractive index and extinction coefficient of compound CBP. As can be seen from FIGS. 3-4, for light having a wavelength in the range of 400 nm to 700 nm, the nitrogen heterocyclic compound of the present disclosure has a refractive index greater than or equal to 2.0. However, for light having a wavelength in the range of 430 nm to 700 nm, the refractive index of the comparative compound CBP is smaller than 2.0. Moreover, the value of the extinction coefficient k of the nitrogen heterocyclic compound of the present disclosure is almost 0 for light having wavelength greater than 450 nm, and thus the nitrogen heterocyclic compound of the present disclosure will not affect luminescence of the material of the light-emitting layer in the region of blue light.

The technical effects achieved by the nitrogen heterocyclic compound of the present disclosure in practical use are illustrated by using the nitrogen heterocyclic compound in an organic light-emitting device.

Example of Organic Light-Emitting Device

Figure 2:
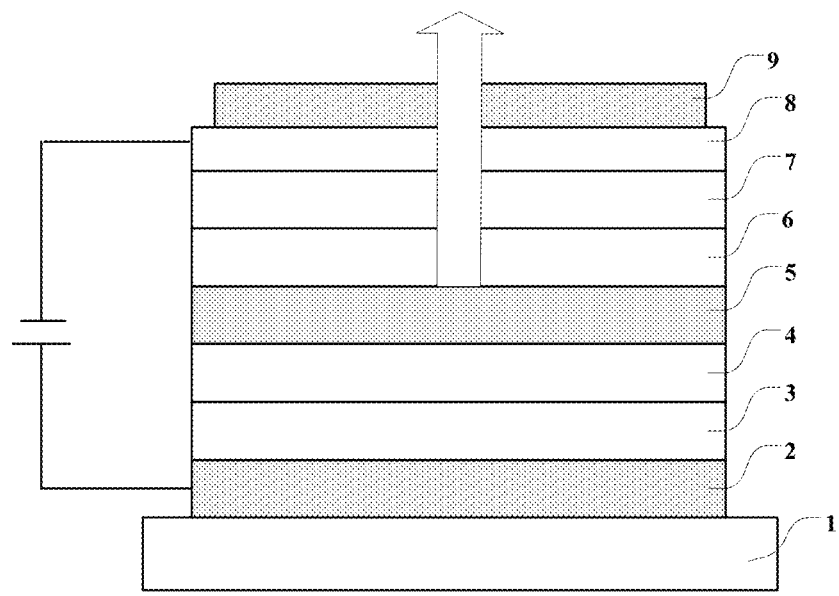
FIG. 2 is a structural schematic diagram showing an OLED device according to an embodiment of the present disclosure.

This example provides an organic light emitting device. As shown in FIG. 2, the organic light-emitting device includes: a substrate 1, an ITO anode 2, a first hole transmission layer 3, a second hole transmission layer 4, a light-emitting layer 5, a first electron transmission Layer 6, a second electron transmission layer 7, a cathode 8 (magnesium silver electrode, a mass ratio of magnesium to silver is 9:1) and a capping layer CPL 9. The ITO anode 2 has a thickness of 15 nm. The first hole transmission layer 3 has a thickness of 10 nm. The second hole transmission layer 4 has a thickness of 110 nm. The light-emitting layer 5 has a thickness of 30 nm. The first electron transmission layer 6 has a thickness of 30 nm. The second electron transmission layer 7 has a thickness of 5 nm. The magnesium silver electrode 8 has a thickness of 15 nm. The capping layer CPL 9 has a thickness of 100 nm.

The steps for preparing the organic light-emitting device according to the present disclosure are as follows.

1) A glass substrate 1 was cut into a size of 50 mm×50 mm×0.7 mm, subjected to ultrasonic treatments in isopropyl alcohol and in deionized water for 30 minutes, respectively, and then exposed to ozone for about 10 minutes for cleaning. The obtained glass substrate with an ITO anode 2 was mounted on a vacuum deposition apparatus.

2) A hole injection layer material HAT-CN was evaporated on the ITO anode layer 2 by vacuum evaporation to a thickness of 10 nm and used as the first hole transmission layer 3.

3) The material TAPC of the second hole transmission layer 2 was evaporated by vacuum evaporation on the first hole transmission layer 3 to a thickness of 110 nm and used as the second hole transmission layer 4.

4) The light-emitting layer 5 was co-deposited on the hole transmission layer 4, where CBP is used as a host material, Ir(ppy)$_3$ is used as a doping material, and a mass ratio of Ir(ppy)$_3$ to CBP is 1:9. The light-emitting layer 5 has a thickness of 30 nm.

5) The material TPBI of the first electron transmission layer 6 was evaporated by vacuum evaporation on the light-emitting layer 5 to a thickness of 30 nm and used as the first electron transmission layer 6.

6) The material Alq3 of the second electron transmission layer 7 was evaporated by vacuum evaporation on the first electron transmission layer 6 to a thickness of 5 nm and used as the second electron transmission layer 7.

7) Magnesium silver electrode was evaporated by vacuum evaporation on the second electron transmission layer 7 to a thickness of 15 nm and used as the cathode 8, in which the mass ratio of Mg to Ag is 9:1.

8) The compound CP2 according to the present disclosure was evaporated by vacuum evaporation on the cathode 8 to a thickness of 100 nm and used as a cathode covering layer (capping layer or CPL) 9.

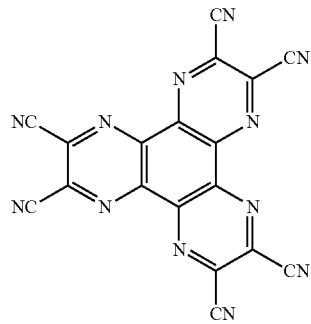

HAT-CN

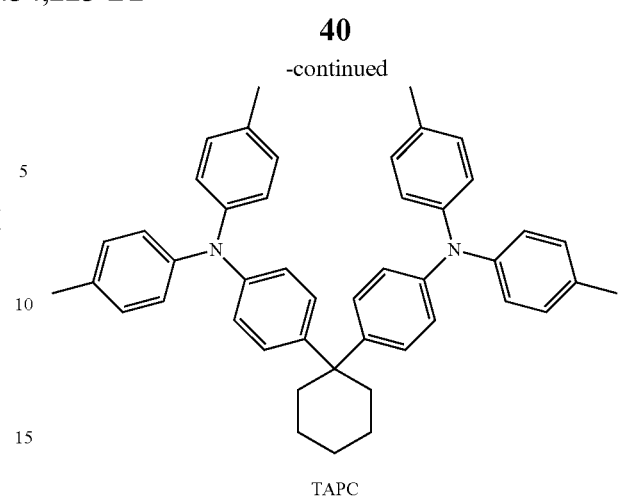

TAPC

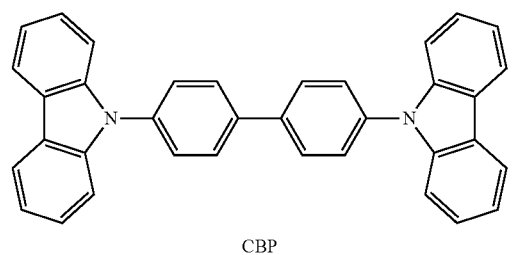

CBP

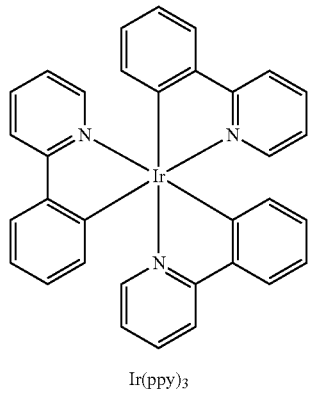

Ir(ppy)$_3$

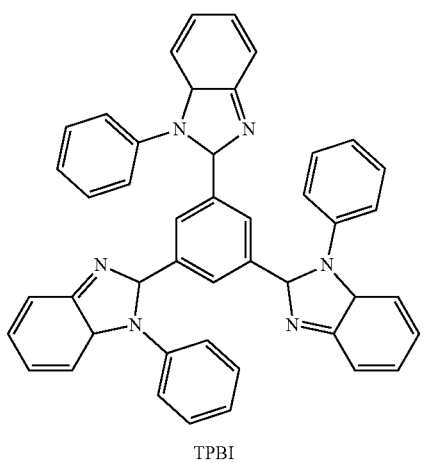

TPBI

-continued

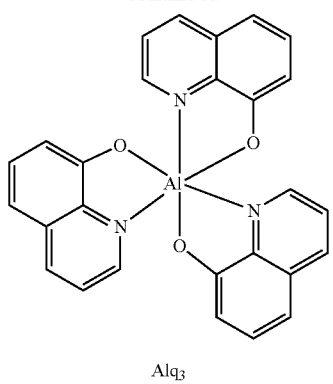

Alq₃

Devices 2-12 were prepared in a same method. In addition, a comparative device 1' was prepared using CBP. The devices prepared here differ from one another only in the material selection of the CPL, and materials of other layers such as the light-emitting layer and the auxiliary layers are the same. The luminescence properties of Devices 1-12 and comparative device 1' were tested. The test results are shown in Table 3.

TABLE 3

Test results of luminescence properties of the devices

| No. | CPL material | Driving voltage (V) | @10 mA/cm² current efficiency (cd/A) | @10 mA/cm² brightness (cd/m²) | Service life (based on comparative example 1) |
|---|---|---|---|---|---|
| device1 | CP1 | 4.3 | 37.4 | 3738.4 | 1.8 |
| device2 | CP2 | 4.3 | 36.8 | 3681.8 | 1.7 |
| device3 | CP4 | 4.3 | 36.9 | 3690.2 | 2.3 |
| device4 | CP8 | 4.2 | 37.2 | 3721.5 | 2.2 |
| device5 | CP11 | 4.3 | 36.8 | 3679.7 | 1.9 |
| device6 | CP14 | 4.4 | 37.1 | 3710.1 | 1.7 |
| device7 | CP20 | 4.3 | 36.9 | 3692.0 | 2.1 |
| device8 | CP21 | 4.2 | 36.8 | 3681.6 | 2.3 |
| device9 | CP30 | 4.3 | 37.5 | 3751.3 | 1.8 |
| device10 | CP35 | 4.2 | 37.3 | 3731.5 | 2.2 |
| device11 | CP42 | 4.3 | 36.7 | 3671.2 | 1.9 |
| device12 | CP62 | 4.4 | 38.1 | 3809.8 | 1.9 |
| comparative device 1' | CBP | 5.1 | 26.9 | 2691.7 | 1 |

As can be seen from the above Table 3, all of the driving voltages of the devices using the nitrogen heterocyclic compound of the present disclosure as a CPL material are lower than that of the comparative device 1'. Current efficiency, brightness (corresponding to light extraction efficiency) and service life of the devices using the nitrogen heterocyclic compound of the present disclosure as a CPL material are significantly improved as compared with the comparative device 1'. Therefore, the nitrogen heterocyclic compound of the present disclosure is an ideal CPL material which can improve the luminous efficiency of the light-emitting device and prolong service life of the device.

Yet another aspect of the present disclosure provides a display panel including the organic light-emitting device provided by the present disclosure.

Yet another aspect of the present disclosure provides a display apparatus including the display panel as described above.

Figure 5:
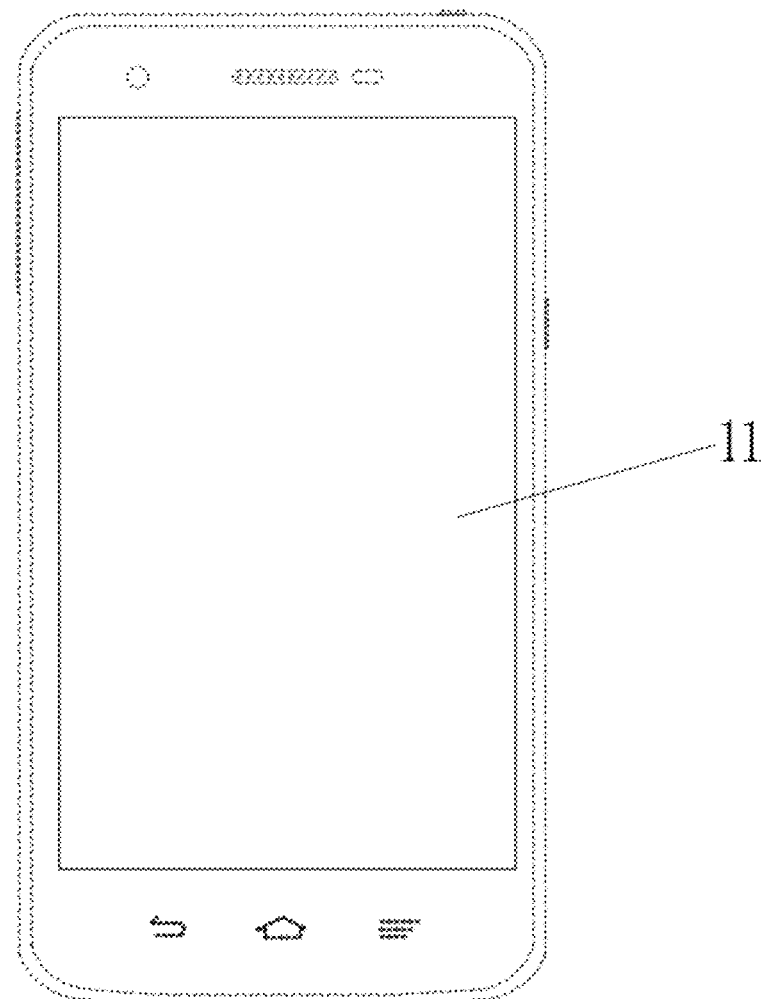
FIG. 5 is a schematic diagram showing a display apparatus according to an embodiment of the present disclosure.

In the present disclosure, the organic light-emitting display apparatus may be a mobile phone display screen, a computer display screen, a liquid crystal television display screen, a smart watch display screen, or a smart car display panel, VR or AR helmet display screen, and display screens of various smart devices, etc. FIG. 5 is a schematic diagram showing a display apparatus according to an embodiment of the present disclosure. In FIG. 5, reference number 11 represents a mobile phone display screen.

The above embodiments are used to illustrate the present disclosure but not intended to limit the scope of the claims. Any change and modification can be made by those skilled in the art without departing from the scope of the present disclosure. The protection scope of the present disclosure is defined by the claims.

What is claimed is:

1. A nitrogen heterocyclic compound having a structure of any one of the following compounds:

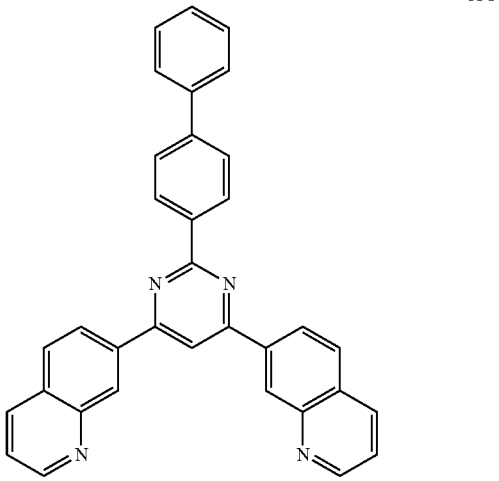

CP1

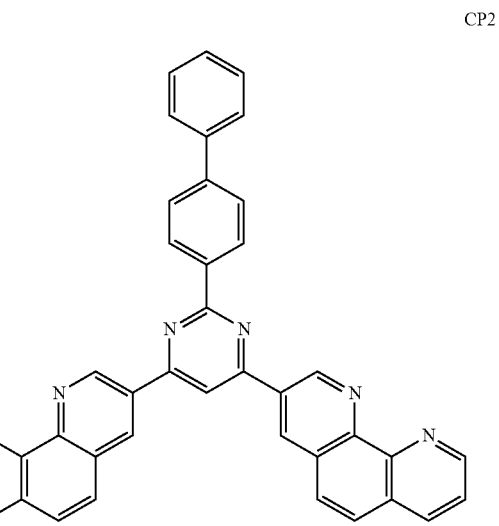

CP2

CP3
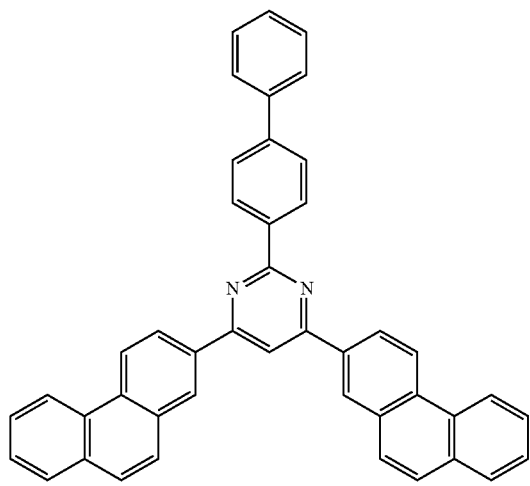
CP6
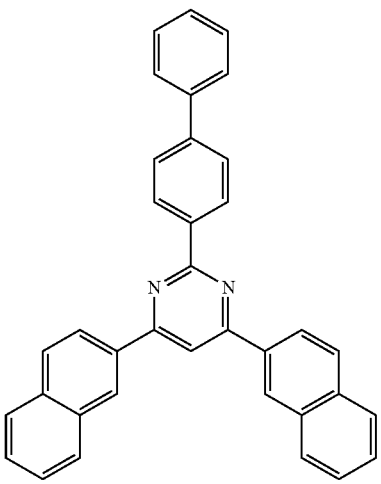
CP4
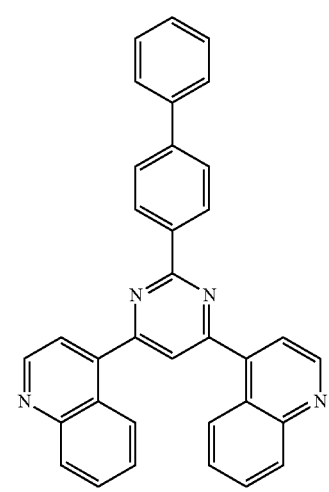
CP8
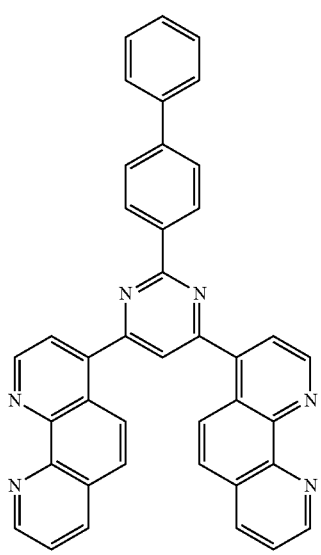
CP5
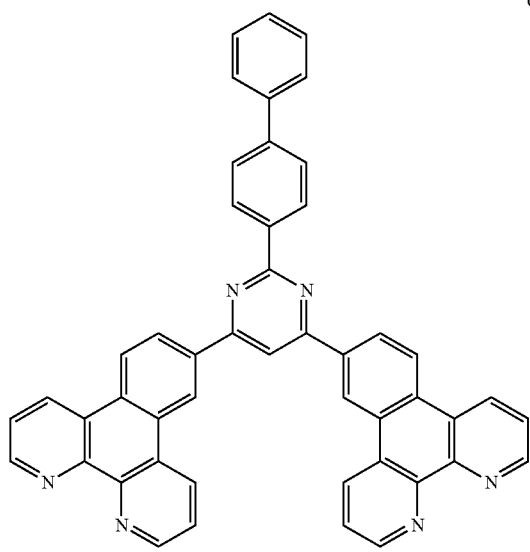
CP10
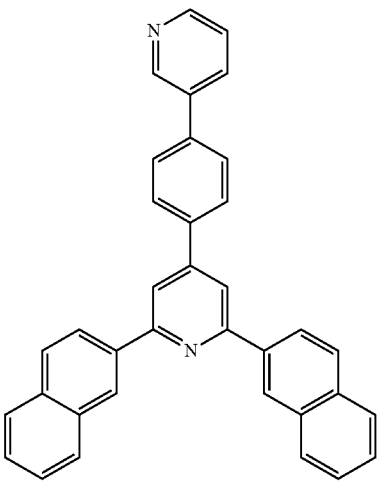

CP13
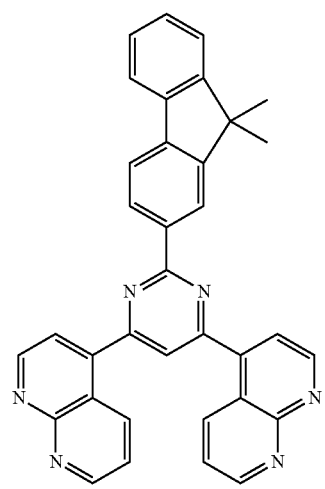
CP14
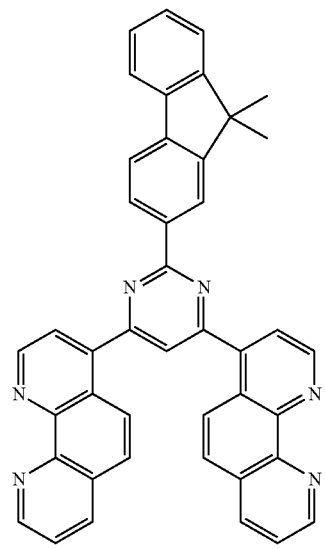
CP16
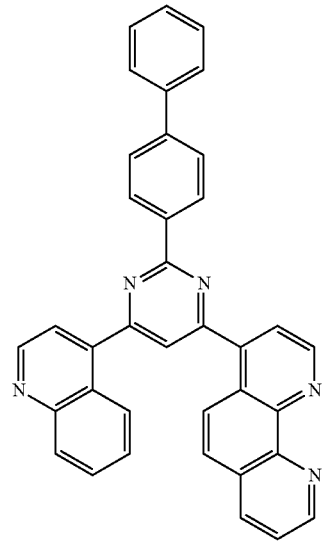
CP17
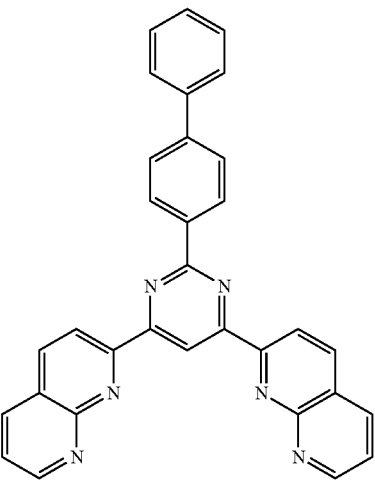
CP18
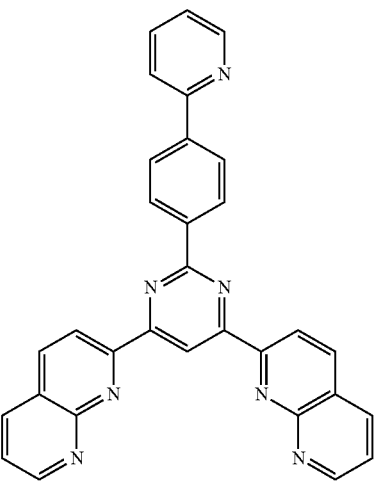
CP19
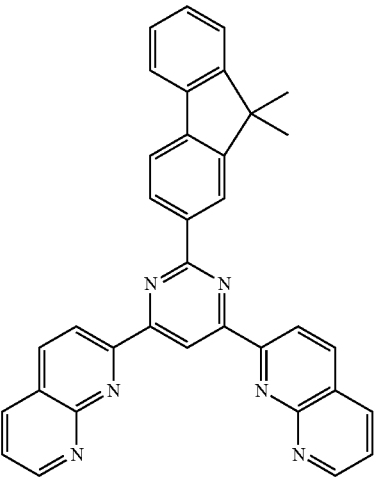

CP20
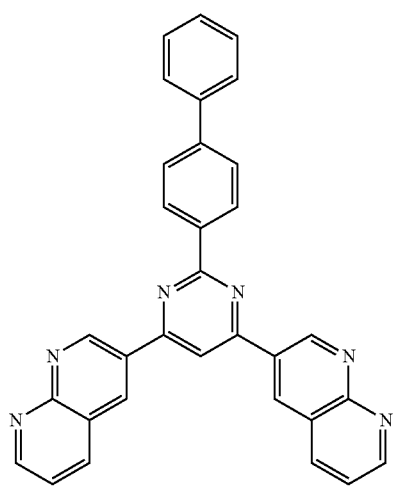
CP21
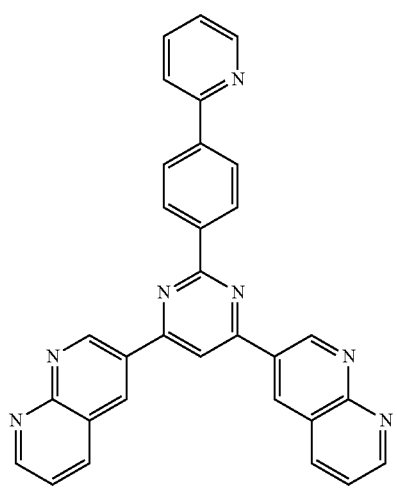
CP22
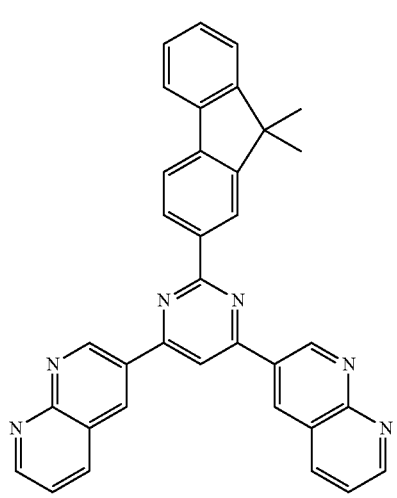
CP23
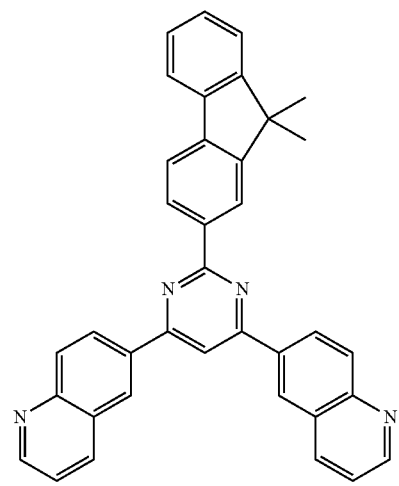
CP24
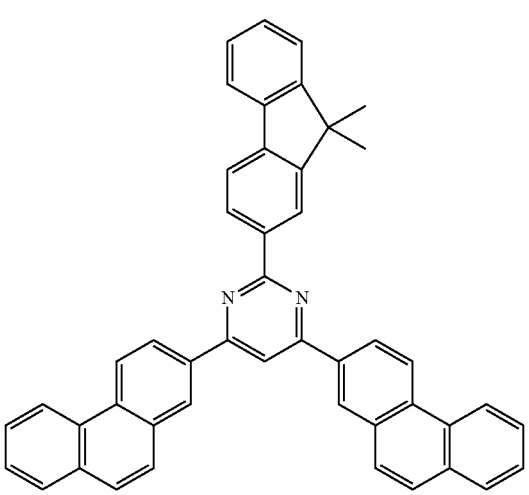
CP25
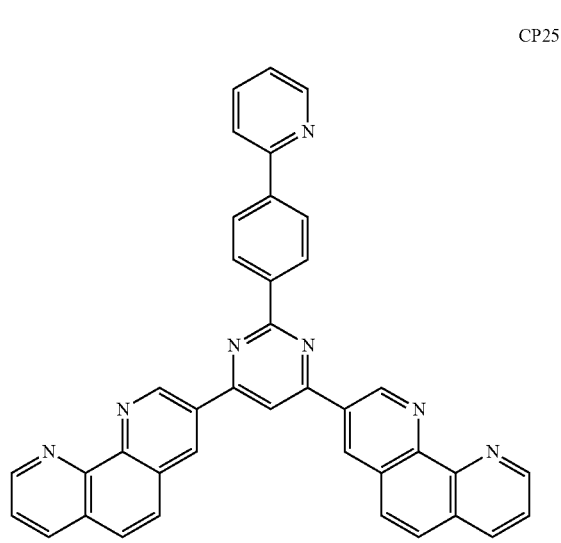 [SMILES: c1cncc(-c2ccc(-c3nc(-c4cnc5c(ccc6cccnc65)c4)cc(-c4cnc5c(ccc6cccnc65)c4)n3)cc2)c1]

CP26
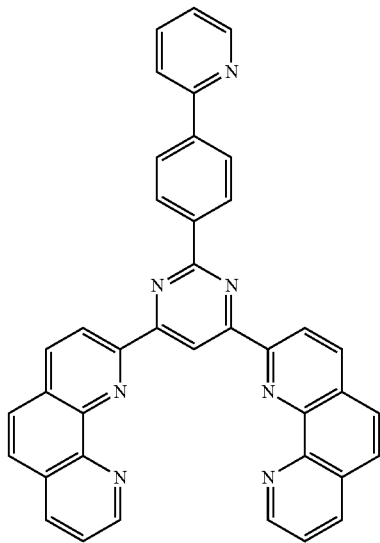
CP27
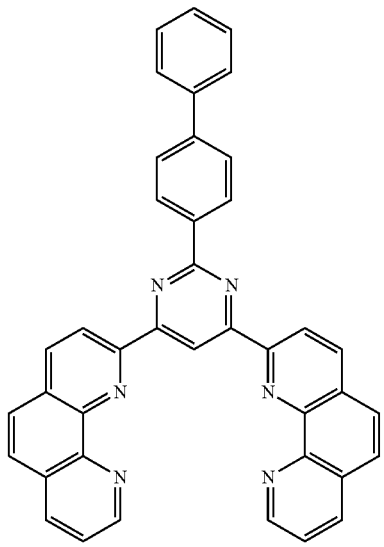
CP28
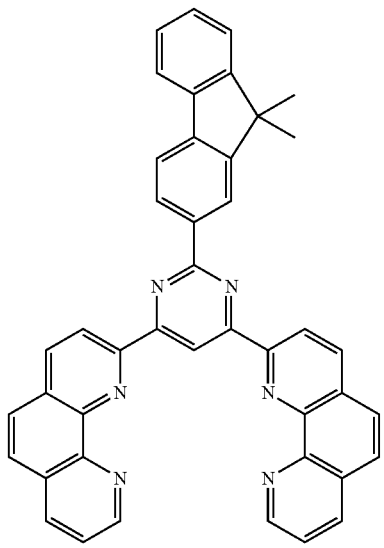
CP29
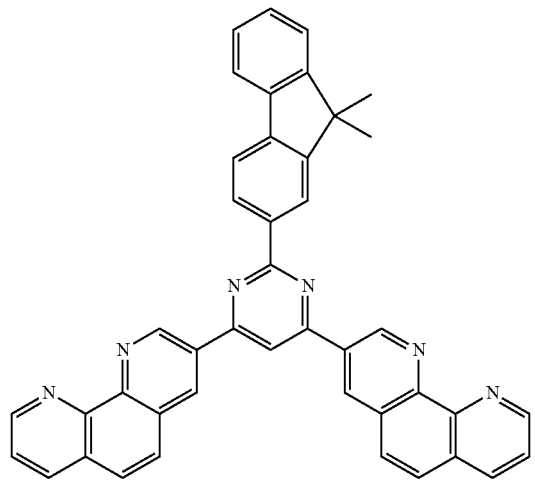
CP30
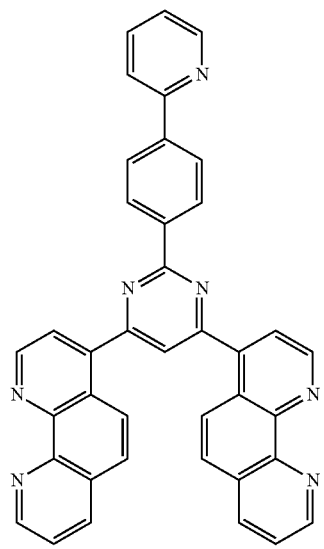
CP31
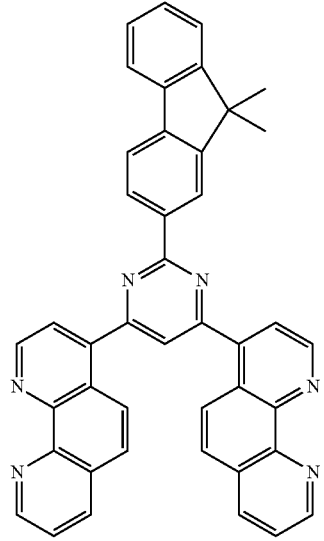

CP34
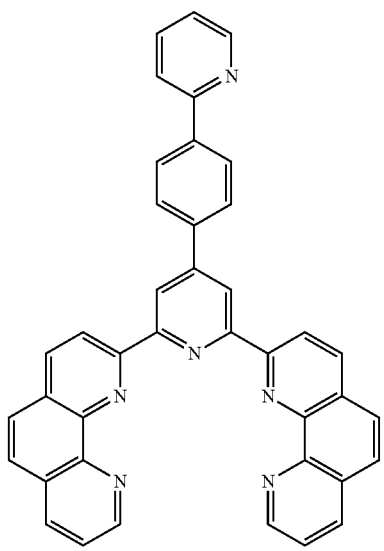
CP36
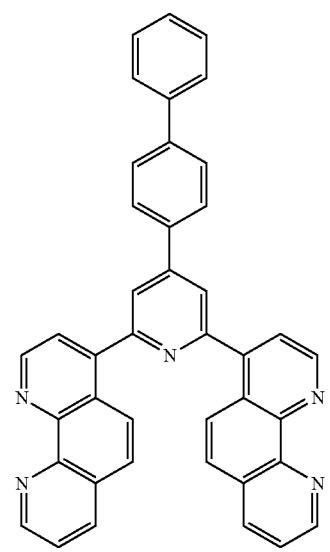
CP37
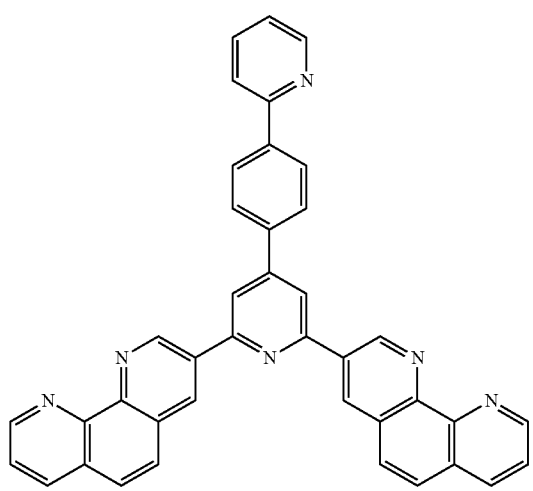
CP38
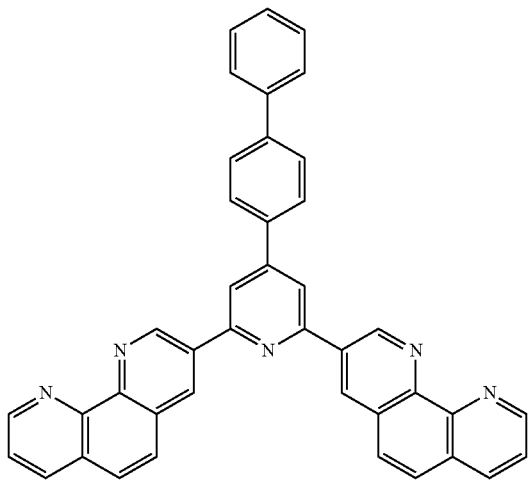
CP39
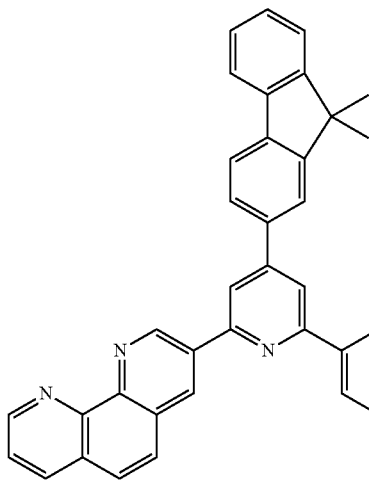
CP40
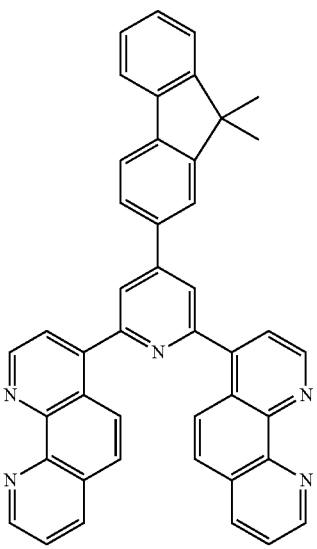

CP41
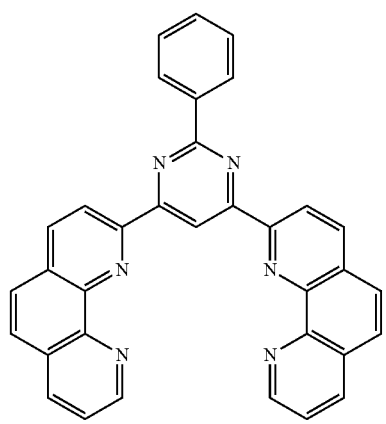
CP42
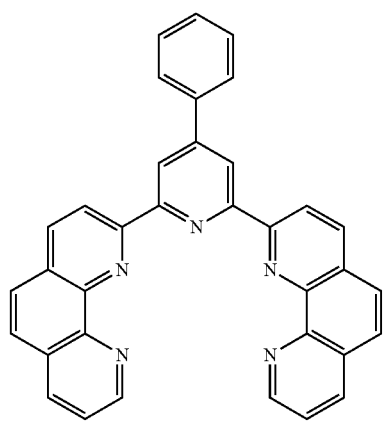
CP43
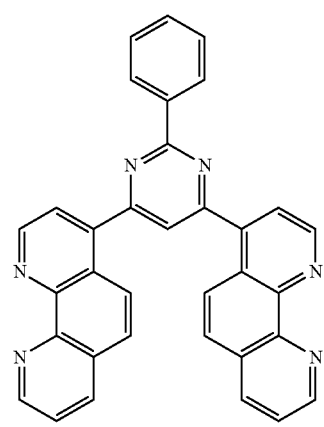
CP44
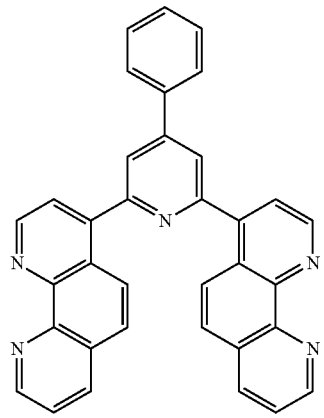
CP45
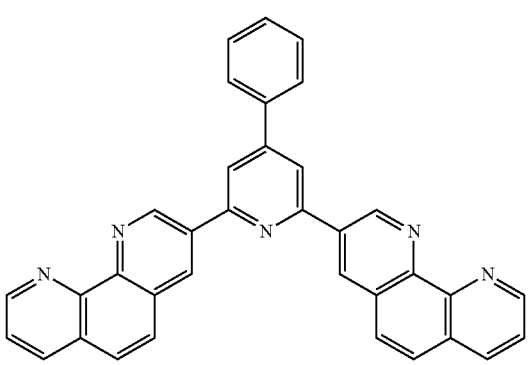
CP46
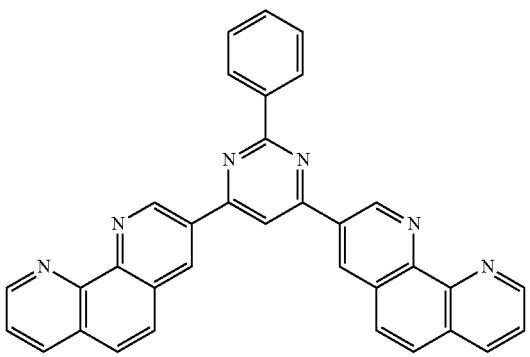

CP49
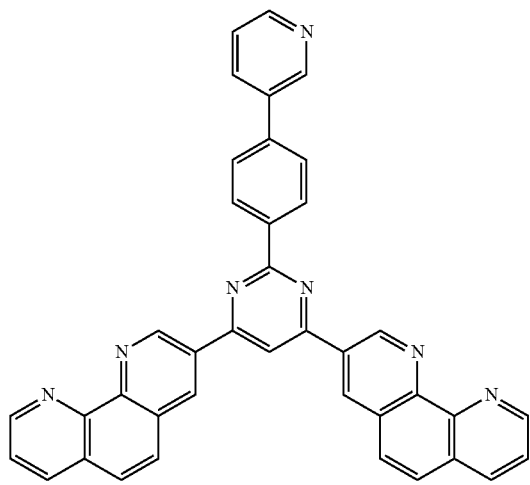
CP50
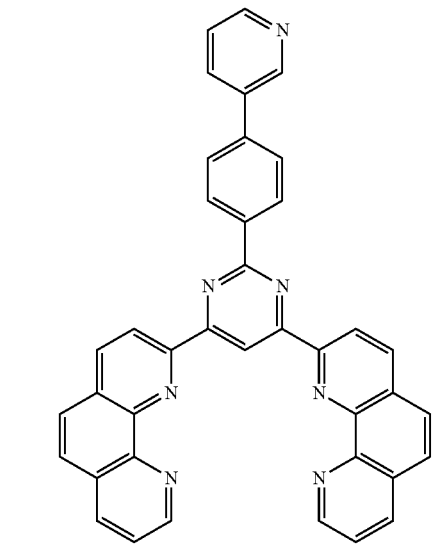
CP51
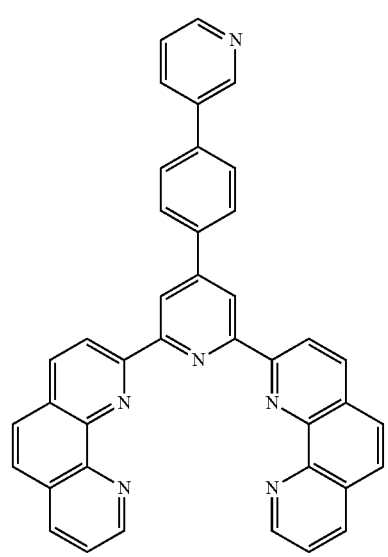
CP52
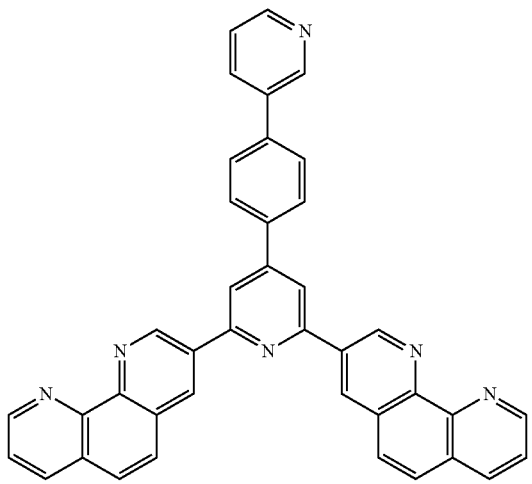
CP53
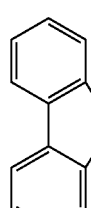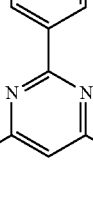
CP54

-continued

CP55

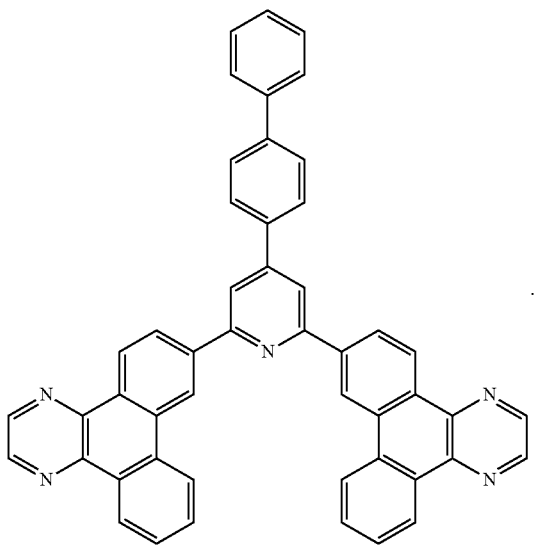

2. The nitrogen heterocyclic compound according to claim 1, wherein a refractive index n of the nitrogen heterocyclic compound is greater than or equal to 2.0 for visible light having a wavelength between 400 nm and 700 nm.

3. The nitrogen heterocyclic compound according to claim 1, wherein an extinction coefficient k of the nitrogen heterocyclic compound is smaller than or equal to 0.0 for visible light having a wavelength between 430 nm and 700 nm.

4. A display panel, comprising an organic light-emitting device, wherein the organic light-emitting device comprises an anode, a cathode arranged opposite to the anode, a capping layer located at a side of the cathode facing away from the anode, and an organic layer located between the anode and the cathode, wherein the organic layer comprises an electron transmission layer, a hole transmission layer, and a light-emitting layer, at least one of the capping layer, the electron transmission layer, the hole transmission layer, and the light-emitting layer is made of the nitrogen heterocyclic compound according to claim 1.

5. The display panel according to claim 4, wherein a stack of the cathode and the capping layer has a transmittance greater than 65% for visible light having a wavelength between 400 nm and 700 nm.

6. A display apparatus comprising the display panel according to claim 4.

* * * * *